US 8,303,947 B2

(12) United States Patent
Wu et al.

(10) Patent No.: US 8,303,947 B2
(45) Date of Patent: Nov. 6, 2012

(54) INOCULATION OF RECOMBINANT VIRAL VECTORS FOR RAPID PRE-EXPOSURE PREVENTION AND POST-EXPOSURE PROTECTION AGAINST ALPHA-VIRUS-INDUCED ENCEPHALITIDES

(75) Inventors: Josh Qiaohua Wu, Medicine Hat (CA); Leslie P. Nagata, Medicine Hat (CA)

(73) Assignee: Her Majesty the Queen in right of Canada, as represented the Minister of National Defence, Ottawa (CA)

(*) Notice: Subject to any disclaimer, the term of this patent is extended or adjusted under 35 U.S.C. 154(b) by 17 days.

(21) Appl. No.: 12/545,933

(22) Filed: Aug. 24, 2009

(65) Prior Publication Data

US 2010/0047274 A1    Feb. 25, 2010

Related U.S. Application Data

(63) Continuation of application No. PCT/CA2008/000343, filed on Feb. 22, 2008.

(60) Provisional application No. 60/902,957, filed on Feb. 23, 2007.

(51) Int. Cl.
*A01N 63/04*    (2006.01)
*C12N 15/79*    (2006.01)

(52) U.S. Cl. .................................. 424/93.6; 435/320.1

(58) Field of Classification Search ........................ None
See application file for complete search history.

(56) References Cited

U.S. PATENT DOCUMENTS

| 6,376,236 B1* | 4/2002 | Dubensky et al. | 435/320.1 |
|---|---|---|---|
| 6,432,699 B1* | 8/2002 | Meruelo et al. | 435/320.1 |
| 6,565,853 B1 | 5/2003 | Jacobs | |
| 6,730,822 B1* | 5/2004 | Ivarie et al. | 800/19 |
| 6,800,289 B2* | 10/2004 | Nagata et al. | 424/207.1 |
| 7,223,409 B2* | 5/2007 | Nagata et al. | 424/207.1 |
| 2006/0147466 A1 | 7/2006 | O'Hagan | |

FOREIGN PATENT DOCUMENTS

| WO | WO 97/42323 | 11/1997 |
|---|---|---|
| WO | WO 98/17801 | 4/1998 |

OTHER PUBLICATIONS

Hunt et al. PloS Negl. Trop, Dis. 2010, vol. 4, pp. 1-12.*
Borden et al. Nature Reviews Drug Discovery 2007, vol. 6, pp. 975-990.*
Sadler et al. Nature Reviews Immunology 2008, vol. 8, pp. 559-568.*
Neumann et al. Science 1998, vol. 282, pp. 103-107.*
Yeow et al. J. Immunology 1998, vol. 160, pp. 2932-2939.*
Kinney et al. J. Virol. 1988, vol. 62 (12), pp. 4697-4701.*
Lukaszewski et al. J. Virol. 2000, vol. 74, No. 11, pp. 5006-5016.*
Tsugawa et al. Gene Therapy (2004) 11, 1551-1558.*
Alberti et al., "Interferon Alfacon-1: A novel Internferon for the Treatment of Chronic Hepatitis C," *Biodrugs* 12: 343-357, 1999.
Appaiahgari et al., "Seroprevalence of Neutralizing Antibodies to Adenovirus Type 5 among Children in India: Implications for Recombinant Adenovirus-Based Vaccines," *Clin. Vacc. Immunol*, 14:1053-1055, 2007.
Blatt, "The Biologic Activity and Molecular Characterization of a Novel Synthetic Interferon-Alpha Species, Consensus Interferon," *J. Interferon Cytokine Res.* 16: 489-499, 1996.
Buchbinder et al., "Efficacy assessment of a cell-mediated immunity HIV-1 vaccine (the Step Study): a double-blind, randomised, placebo-controlled, test-of-concept trail," *Lancet* 372:1881-1893, 2008.
Chinsangaram, "Novel Viral Disease Control Strategy: Adenovirus Expressing Alpha Interferon Rapidly Protects Swine from Foot-and-Mouth Disease," *Journal of Virology* 77:1621-1625, 2003.
Croyle et al., "Nasal Delivery of an Adenovirus-Based Vaccine Bypasses Pre-Existing Immunity to the Vaccine Carrier and improves the Immune Response in Mice," *PLoS One 3*: e3546, 2008.
Dart, Medical Toxicology, 3rd Edition. Lippincott, Williams & Williams, p. 512, 2004.
Demers et al., "Interferon-2b Secretion by Adenovirus-Mediated Gene Delivery in Rat, Rabbit, and Chimpanzee Results in Similar Pharmacokinetic Profiles" Tox. Apple. Pharm. 180:36-42, 2002.
Gowen et al., "Extended Protection Against Phlebovirus Infection Conferred by Recombinant Adenovirus Expressing Consenus Interferon (DEF201)," *Antimicrob.* Ag. Chem., 2012, in press.
Gowen et al., "Use of Recombinant Adenovirus Vectored Consensus IFN-a to Avert Severe Arenavirus Infection," *PLos One* 6:e26072, 2011.
Grubb et al., "Inefficient gene transfer by adenovirus vector to cystic fibrosis airway epithelia of mice and humans," *Nature* 371:802-806, 1994.
Gutierro, "Influence of dose and immunization route on the serum Ig G antibody response to BSA loaded PLGA microspheres," *Vaccine*, 20:2181-2190, 2002.
Hahn et al., "Western equine encephalitis virus is a recombinant virus," *Proc. Matl. Acad. Sci. USA.* 85: 5997-6001, 1988.
Hangaiapura et al., "Delivery route, MyD88 signaling and cross-priming events determine the anti-tumor efficacy of an Adenovirus based melanoma vaccine," *Vaccine* 29: 2313-2321, 2011.
Huang, "A novel dry powder influenza vaccine and intranasal delivery technology: induction of systematic and mucosal immune responses in rats," *Vaccine*, 23:794-801, 2006.
Isaacs and Lindenmann, "Virus Interference. I. The Interferon," *Proc. R. Soc. Lond*. 147:258, 1957.
Jolly, "Adenoviral Vectors: History and Perspective," Chapter 4, Concepts in Medicine, p. 39-54, Wiley-Liss, 2008.
Julander et al., "Treatment of Yellow Fever Virus with an Adenovirus-Vectored Interferon, DEF201, in a Hamster Model," *Antimicrob. Agents Chemother.* 55:2067-2073, 2011.
Keedy et al., "Phase I study of adenovirus p53 administered by bronchoalveolar lavage in patients with bronchioloalveolar cell lung carcinoma: ECOG 6597," *J. Clin. Oncol.* 26:4166-4171, 2008.

(Continued)

*Primary Examiner* — Bao Li
(74) *Attorney, Agent, or Firm* — Clark & Elbing LLP; Todd Armstrong

(57) ABSTRACT

This invention addresses how to rapidly prevent alphavirus-induced encephalitides before and after exposure to alphaviruses. The invention discloses a single dose administration of two types of recombinant viral vectors: one expressing interferon and another expressing the structural proteins of alphaviruses or a single dose administration of the recombinant viral vector co-expressing both interferon and the structural proteins of alphaviruses. This invention can be used to prevent humans from alphavirus-induced encephalitides in the event of a bioterrorism attack or biowarfare in which alphaviruses such as Venezuelan (VEEV), eastern (EEEV) and western (WEEV) equine encephalitis viruses are deliberately released to humans, a natural outbreak of alphaviruses, and an accidental exposure to alphaviruses in laboratory.

6 Claims, 10 Drawing Sheets

OTHER PUBLICATIONS

Knowles, "A controlled study of adenoviral-vector-mediated gene transfer in the nasal epithelium of patients with cystic fibrosis," *New England J. Med.* 333:823-832, 1995.

Kumaki et al., "Single-dose intranasal administration with mDEF201 (adenovirus vectored mouse interferon-alpha) confers protection from mortality in a lethal SARS-CoV BALB/c mouse model," *Antiviral Res.* 89:75-82. 2011.

Lukasewski et al., "Pegylated Alpha Interferon Is an Effective Treatment for Virulent Venezuelan Equine Encephalitis Virus and has Profound Effects on the Host Immune Response to Infection," *Journal of Virology*. 74: 5006-5015, 2000.

Moraes, "Immediate protection of swine from foot-and-mouth disease: a combination of adenoviruses expressing interferon alpha and a foot-and-mouth disease virus subunit vaccine," Vaccine. 22:268-279, 2003.

Moraes, "pAd5-Blue: Direct Ligation System for Engineering Recombinant Adeno-virus Constructs." Biotechniques, 31:1050-1056, 2001.

Nagata et al., "Infectivity variation and genetic diversity among strains of *Western equine encephalitis virus,*" Journal of General Virology, 87: 2353-2361, 2006.

NIH Report, "Assessment of Adenoviral Vector Safety and Toxicity: Report of the National Institutes of Health Recombinant DNA Advisory Committee," *Hum. Gene Therap.* 13:3-13, 2002.

Pickles et al., "Retargeting the Coxsackievirus and Adenovirus Receptor to the Apical Surface of Polarized Epithetial Cells Reveals the Glycocalyx as a Barrier to Adenovirus-Medicated Gene Transfer," *J. Virol.* 74:6050-6057, 2002.

Pickles et al., "Utility of Adenoviral Vectors in Animal Models of Human Disease II: Genetic Disease," In: Adenoviral Vectors for Gene Therapy. Elsevier Science p. 565-594, 2002.

Priddy et al, "Safety and Immunogenicity of a Replication-Incompetent Adenovirus Type 5 HIV-1 Clade B gag/pol/nef Vaccine in Healthy Adults," *Clin. Infect. Dis.* 46:1769-1781, 2008.

Reid et al., "Intra-arterial Administration of a replication-selective adenovirus (dl1520) in patients with colorectal carcinoma metastatic to the liver a phase I trial," *Gene Therapy* 8(21): 1618-1626, 2001.

Richardson et al., "Enhanced Protection against Ebola Virus Mediated by an Improved Adenovirus-Based Vaccine," *PLoS ONE*, 4:e530808, 2009.

Smee et al., "Therapy and Long-Term Prophylaxis of Vaccinia Virus Respiratory Infections in Mice with an Adenovirus-Vectored interferon Alpha (mDEF201)," *PLoS One* e26330, 2011.

Sullivan, "Development of a preventive vaccine for Ebola virus infection in Primates," *Nature*, 408:605-609, 2000.

Sumida et al. "Neutralizing Anitbodies to Adenovirus Serotype 5 Vaccine Vectors Are Directed Primarily against the Adenovirus Hexon Protein," *J. Immunol.* 174:7179-7185, 2005.

Thomas et al., "Progress and problems with the use of viral vectors for gene therapy," *Nat. Rev. Gen.* 4:346-358, 2003.

Tsai, T.F., et al., "Alphaviruses," *Clinical Virology* , 2:1177-1210, 2002.

Walters et al., "Basolateral localization of fiber receptors limits adenovirus infection from the apical surface of airway epithelia," *J. Biol. Chem* . 274:10219-10226, 1999.

Wu et al., "Adenovirus-mediated type I interferon expression delays and reduces disease signs in cattle challenged with foot-and-mouth disease virus." J. Interferon Cytokine Res. 23:359-368, 2003.

Zuckerman et al., "A Phase I Study of Adenovirus-Mediated Transfer of the Human Cystic Fibrosis Transmembrane Conductance Regulator Gene to a Lung Segment of Individuals with Cyslic Fibrosis," *Human Gene Therapy* 10:2973-2985, 2004.

Office Action. U.S. Appl. No. 12/797,575, dated Feb. 24, 2012.

\* cited by examiner

Figure 2

Figure 3
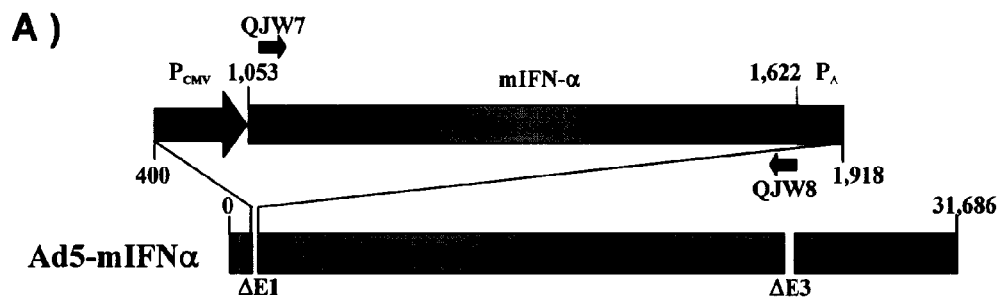
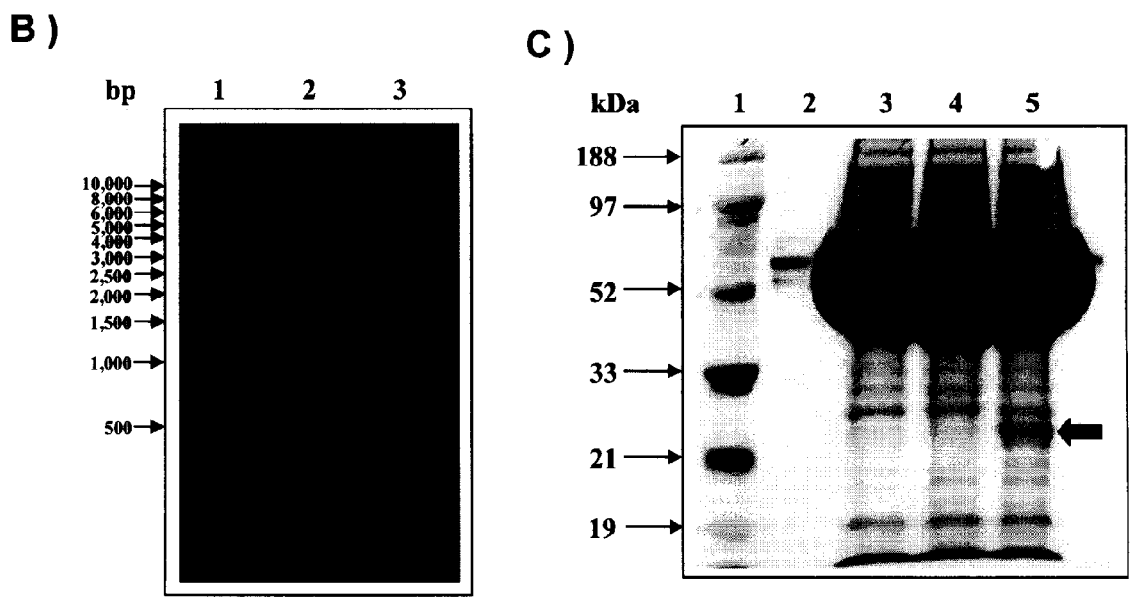
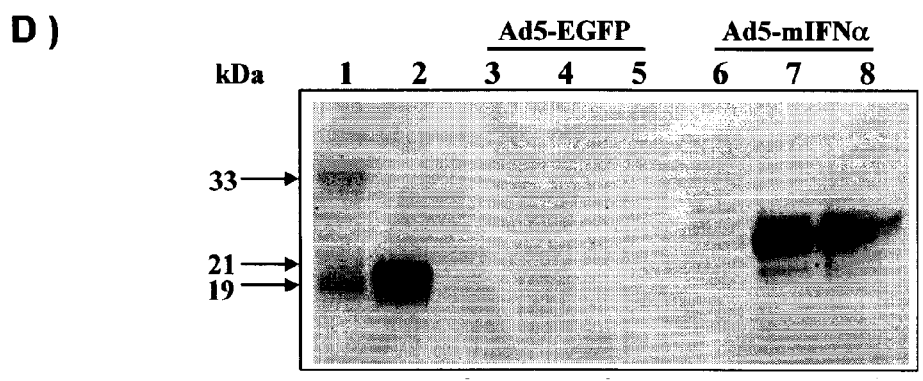

Figure 4
A)
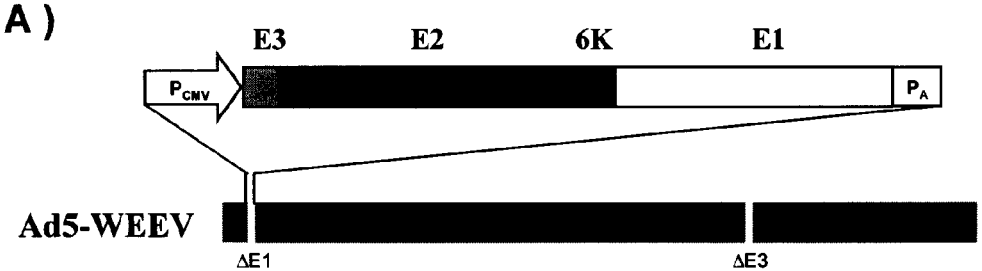
B)
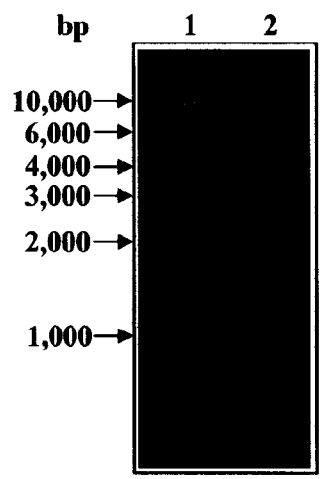
C)
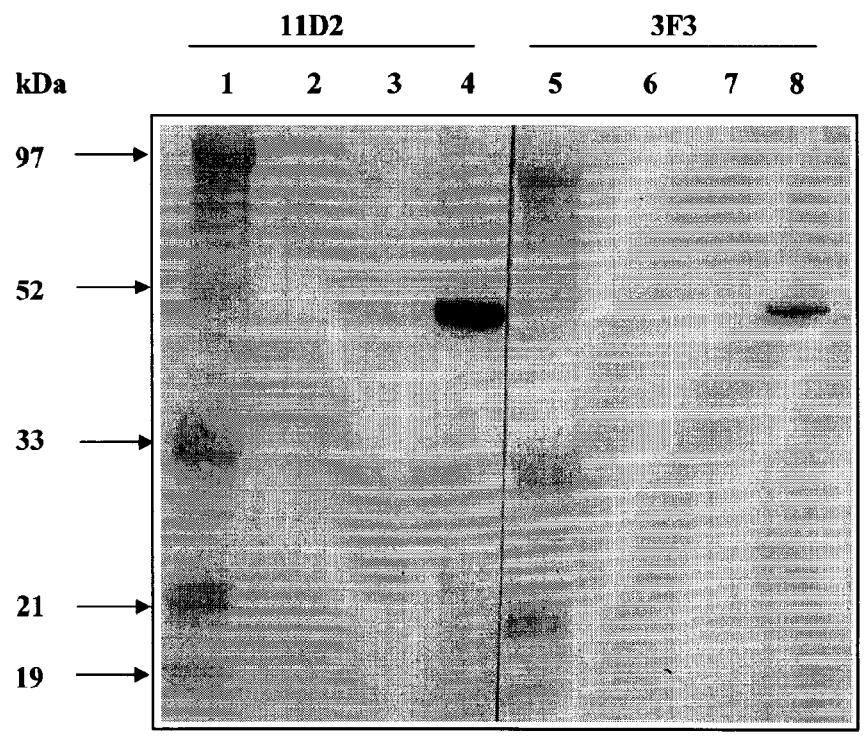

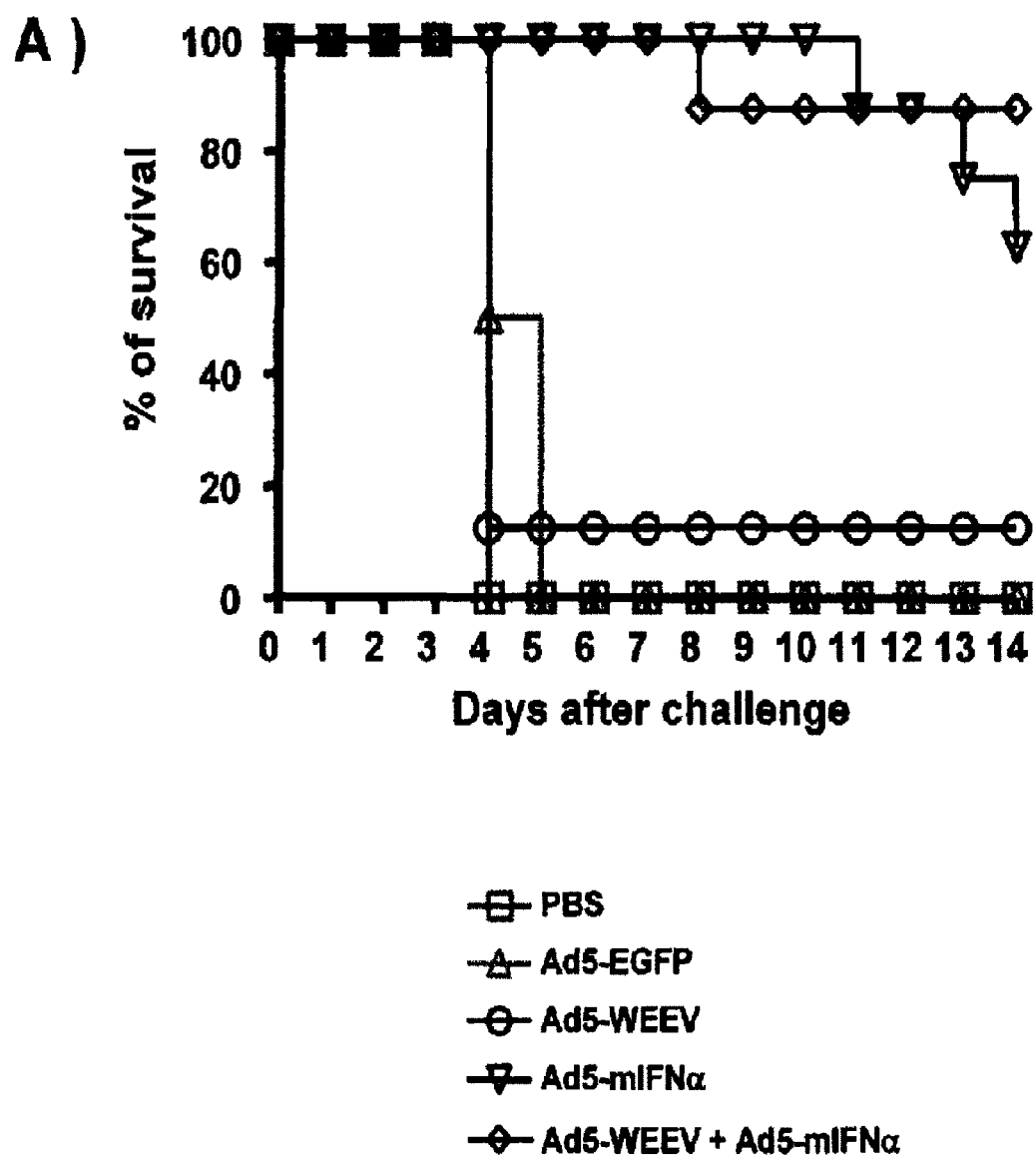
Figure 5 (1/3)

Figure 5 (2/3)

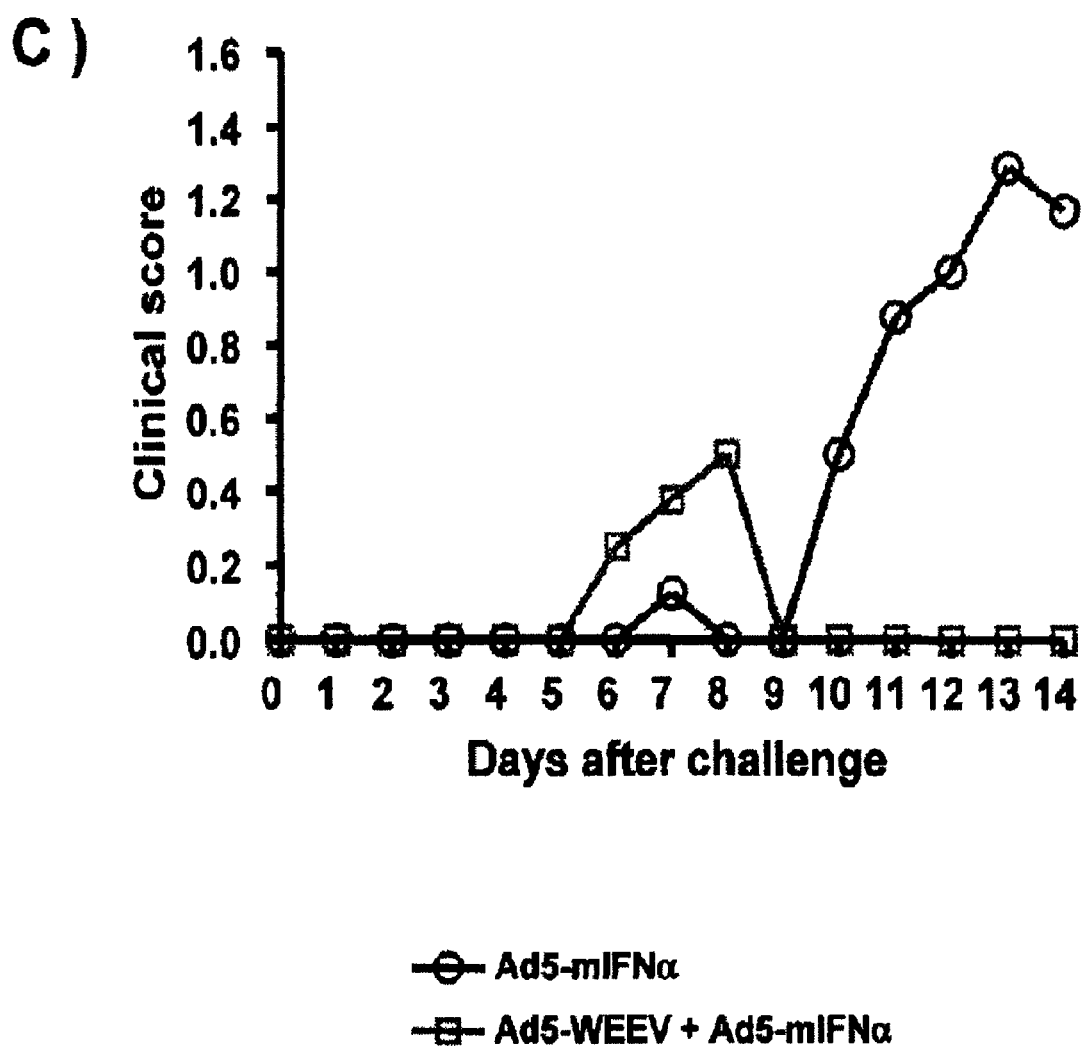
Figure 5 (3/3)

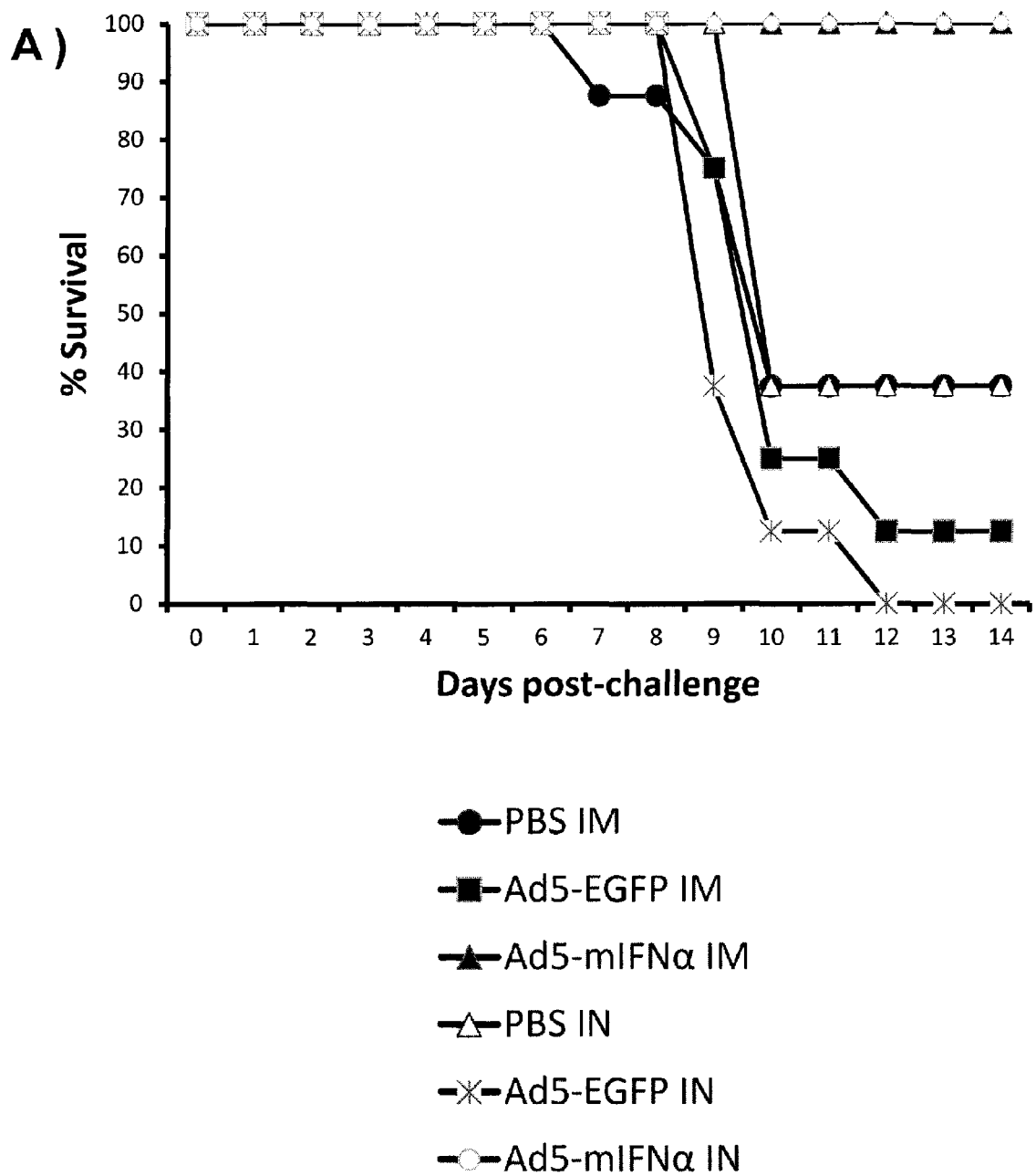

Figure 6 (2/2)
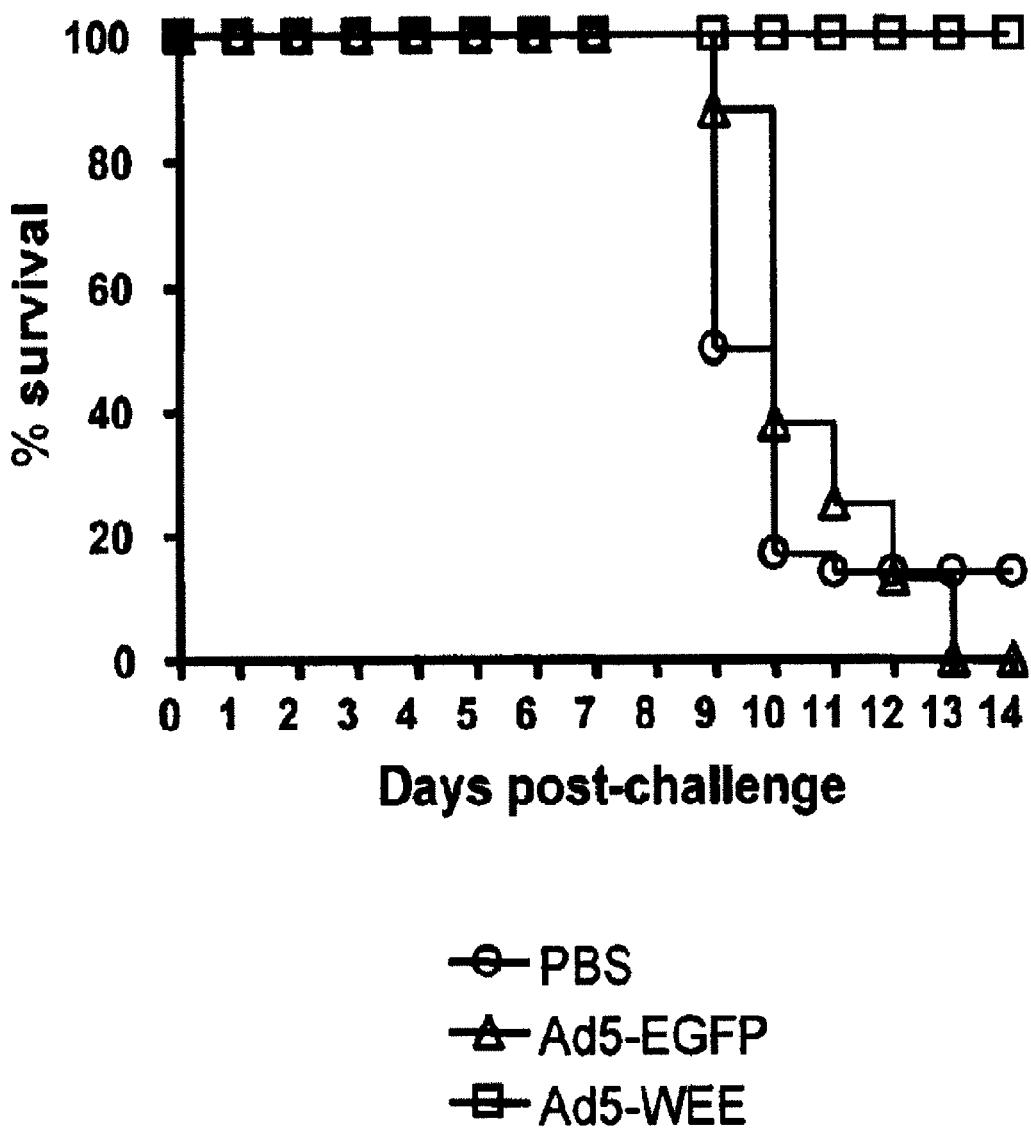

INOCULATION OF RECOMBINANT VIRAL VECTORS FOR RAPID PRE-EXPOSURE PREVENTION AND POST-EXPOSURE PROTECTION AGAINST ALPHA-VIRUS-INDUCED ENCEPHALITIDES

This application is a continuation under 35 U.S.C. §120 of PCT/CA2008/000343, filed Feb. 22, 2008, and which claims priority under 35 U.S.C. §119(e) to U.S. Provisional Patent Application No. 60/902,957 filed on Feb. 23, 2007, which are incorporated in their entireties by reference.

BACKGROUND OF THE INVENTION

1. Field of the Invention

This invention relates to rapid protection against alphavirus-induced encephalitides before or after exposure to alphaviruses. The protection can be achieved by the administration of a single dose, fast-acting vaccine comprising recombinant viral vectors expressing the structural proteins of alphaviruses or by the administration of a single dose recombinant viral vectors expressing interferon. Alternatively, the rapid pre- or post-exposure protection can be achieved by a single dose, simultaneous administration of the vaccine and the interferon delivered by the recombinant viral vectors or by a single dose administration of recombinant viral vectors co-expressing both the structural proteins of alphaviruses and interferon.

2. Brief Description of the Related Art

Alphavirus-induced encephalitides are caused by Venezuelan (VEEV), eastern (EEEV) and western (WEEV) equine encephalitis viruses (Griffin, 2001). The disease is characterized by fever, persistent headache, confusion, agitation, difficulty waling, and seizures. In severe cases, persistent neurological damage and death may occur. VEEV, EEEV, and WEEV cause encephalitides in humans with different fatality rates. EEEV is the most virulent with case fatality rates of 30% to 40%. In fatal cases, patients usually die within 2 to 10 days after the onset of encephalitis. Compared to EEEV, WEEV appears to be less virulent with case fatality rates of 10%. The fatal encephalitis often occurs in infants and in young children. VEEV usually causes an acute incapacitating illness with fever, chills, headache, muscle pain, diarrhea and vomiting. The encephalitis occurs usually in children with a case fatality rate of less than 1%. Besides fatal encephalitides in humans, VEEV, EEEV and WEEV also cause outbreaks of the disease in equines and other domestic animals with high death rates. Therefore, these viruses are important emerging and reemerging human and veterinary pathogens.

The structure of alphaviruses consists of a protein coat termed envelope, a capsid, and inside the capsid, a positive-sense, single-stranded RNA genome (Schlesinger and Schlesinger, 2001). The 5' two thirds of the viral RNA genome encodes the nonstructural proteins required for transcription and replication of the viruses. The 3' one third of the viral genome encodes the capsid and envelope proteins. The envelope proteins are encoded by a subgenomic mRNA and derived by the proteolytic cleavage of the E3-E2-6K-E1 polypeptide into the E2 and E1 proteins (Strauss and Strauss, 1994). E2 protein binds to E1 to form the spikes on the surface of the virion. The E2 and E1 proteins of alphaviruses trigger host immune responses against the viruses (Das et al., 2004; Hodgson, Ludwig, and Smith, 1999; Mathews and Roehrig, 1982).

VEEV, EEEV, and WEEV are transmitted by mosquitoes. Natural outbreaks of the disease occur when humans or domestic animals are bitten by mosquitoes carrying the viruses. There are no human-to-human transmissions of the viruses. Therefore, humans are considered to be dead-end hosts. Outbreaks of alphavirus-induced encephalitides can have enormous impact on human health. For instance, an outbreak of VEEV in Venezuelan and Colombia in 1995 caused more than 75,000 cases with 300 deaths reported (Weaver et al., 1996). About 1,000 human cases were recorded in 1941 in a major outbreak of WEEV occurred in western Canada (Reisen and Monath, 1989).

Besides natural outbreaks, VEEV, EEEV, and WEEV are potential bioterrorism and biowarfare agents because they are highly infectious through the aerosol transmission. For example, only 10 to 100 of the aerosolized VEEV are sufficient for infection and at least 150 human cases of laboratory acquired infections have been reported (Sidwell and Smee, 2003). The U.S. Centers for Disease Control and Prevention (CDC) has classified VEEV, EEEV, and WEEV as category "B" bioterrorism agents.

Currently, there were no vaccines, antiviral drugs or therapeutics for rapid pre-exposure prevention or post-exposure protection against alphavirus-induced encephalitides. For pre-exposure prevention, a live attenuated VEEV vaccine, designated as TC-83, has been developed. The vaccine protects laboratory workers from the VEEV infection. However, 15% to 30% of vaccine recipients developed fever, malaise and headache and these side-effects are so severe that bed rest was required in about the half of vaccine recipients (Hoke, 2005). Killed EEEV and WEEV vaccines with Investigational New Drug (IND) status are available only for laboratory workers at the risk of exposure to these viruses. However, to be effective, these EEEV and WEEV vaccines require multiple injections and annual booster. Therefore, improved vaccines are needed for the rapid pre-exposure prevention of alphavirus-induced encephalitides.

Because no antiviral drugs or therapeutics are available for post-exposure protection against alphavirus-induced encephalitides, the treatment focuses on easing clinical symptoms using antihyperthermia procedures for fever and anticonvulsant drugs.

Several strategies have been proposed for post-exposure protection against alphavirus-induced encephalitides. The first is the use of mouse monoclonal antibodies (mAbs) that neutralize alphaviruses. Such mAbs protected approximately 50% mice against VEEV infection when given 24 h after the airborne challenge with the virulent VEEV (Phillpotts, 2006; Phillpotts, Jones, and Howard, 2002). Because mouse mAbs are highly immunogenic in humans and are not suitable for human use, these mouse mAbs are humanized by replacing much of amino acid sequence of mouse mAbs with those of humans. Ninety percent of the VEEV infected mice were cured after they were given the humanized mAbs within 1 h after exposure to VEEV and 75% of mice were cured after they were given the humanized mAbs 24 h after the virus exposure (Hunt et al., 2006). However, a drawback of using mAbs for post-exposure protection against alphavirus-induced encephalitides is that a large quantity of purified mAbs is required. For instance, as much as 4 mg/kg mAbs is needed to protect 50% of mice from VEEV infection (Phillpotts, Jones, and Howard, 2002). Although mAbs against WEEV have been developed (U.S. Pat. No. 6,812,329) (Long et al., 2000a; Long et al., 2000b; Yamamoto et al., 1985), there have been no reports regarding their protection of animals against WEEV infection.

Another strategy for post-exposure protection against alphavirus-induced encephalitides is the use of interferon alpha (IFN-α). IFN-α is produced by cells immediately after virus infection. It inhibits the replication of a wide-spectrum of viruses by inducing cells to synthesize various antiviral proteins. U.S. patent application Ser. No. 11/231,433 (Publication Number US2006/0024270) discloses methods for treating patients with viral encephalitides by injection of IFN-α. Compared to patients that did not receive IFN-α, patients given IFN-α resulted in a significantly improved neurologic function and survival. However, clinical use of IFN-α for viral encephalitides is limited by the requirement of frequent injections (typically every 24 h for up to 14 days) with a large dose of IFN-α (3 million units) and toxicities associated with IFN-α, which include a flu-like syndrome with fever, malaise and headache. Conjugating IFN-α with polyethylene glycol (PEG) prolongs the in vivo half-life of IFN-α and its potency. For instant, pre-exposure treatment of mice with PEG-conjugated IFN-α prevented mice from either a subcutaneous or an aerosol challenge of VEEV while pre-exposure treatment of unmodified IFN-α did not (Grieder and Vogel, 1999; Lukaszewski and Brooks, 2000). However, there are no reports to define if PEG-conjugated IFN-α could protect mice from encephalitides after the exposure to VEEV, WEEV or EEEV.

Several experimental vaccines for VEEV, EEEV and WEEV have been developed for the prevention of alphavirus-induced encephalitides. However, no data have been shown that these experimental vaccines are effective for post-exposure protection. U.S. Pat. No. 6,261,570 describes the construction of live attenuated vaccines for these alphaviruses. A single dose injection of these vaccines protected animals from the challenge of the viruses. However, concerns of side effects and the reversion to the virulence wild-type viruses may prevent their use in humans. A DNA vaccine candidate for WEEV completely protected mice from the challenge of WEEV (Nagata et al., 2005). Similar to the killed WEEV vaccine, however, the DNA vaccine candidate requires three injections to be effective. Several groups demonstrated that viral-vectored VEEV vaccines protected mice from VEEV challenge (Paessler et al., 2006; Perkins, O'Brien, and Phillpotts, 2006; Phillpotts et al., 2005; U.S. Pat. No. 6,936,257). U.S. Pat. No. 6,565,853 teaches an adenovirus which encodes a polypeptide which produces a protective immune response against an alphavirus, such as a VEEV, when administered to a mammal.

Finally, several anti-alphavirus drug candidates have been developed. For instance, Poly ICLC, a nucleic acid-based immunomodulator, induces interferon production and activates natural killer cells. Liposomes encapsulated poly ICLC offers 100% protection against a lethal intranasal challenge of WEEV (Wong et al., 2005). However, no data have been reported on post-exposure protection. Other drug candidates such as triaryl pyrazolin (Puig-Basagoiti et al., 2006), ribozyme (Seyhan et al., 2002), the zinc-finger antiviral protein (Bick et al., 2003), and human lactoferrin (Waarts et al., 2005) inhibit alphavirus replication in a cell culture system; however, it is unknown if these drug candidates are effective in the prevention or treatment of alphavirus-induced encephalitides in animals.

Thus, this invention addresses two important aspects of medical countermeasures against alphaviruses: one is to rapidly prevent alphavirus-induced encephalitides before exposure to the viruses and another is to rapidly protect against alphavirus-induced encephalitides after exposure to the viruses. The present invention can be used to prevent the encephalitides should the following scenarios occur: a bioterrorism attack or a biowarfare in which the viruses are deliberately released to the public or to military personnel, a natural outbreak of VEEV, or EEEV or WEEV, and a laboratory accident in which the laboratory workers are at the risk of exposure to these viruses.

LIST OF PRIOR ART LITERATURES

Bartelloni, P. J., McKinney, R. W., Calia, F. M., Ramsburg, H. H., and Cole, F. E., Jr. (1971). *Am J Trop Med Hyg* 20(1), 146-9.

Bick, M. J., Carroll, J. W., Gao, G., Goff, S. P., Rice, C. M., and MacDonald, M. R. (2003). *J Virol* 77(21), 11555-62.

Chartier, C., Degryse, E., Gantzer, M., Dieterle, A., Pavirani, A., and Mehtali, M. (1996). *J Virol* 70(7), 4805-10.

Das, D., Gares, S. L., Nagata, L. P., and Suresh, M. R. (2004). Evaluation of a Western *Antiviral Res* 64(2), 85-92.

Grieder, F. B., and Vogel, S. N. (1999). *Virology* 257(1), 106-18.

Griffin, D. E. (2001). Alphaviruses. 4th ed. In "Fields Virology" (D. M. Knipe, and P. M. Howley, Eds.), Vol. 2, pp. 2265-2300. 2 vols. Lippincott Williams & Wilkins, Philadelphia.

He, T. C., Zhou, S., da Costa, L. T., Yu, J., Kinzler, K. W., and Vogelstein, B. (1998). *Proc Natl Acad Sci USA* 95(5), 2509-14.

Hodgson, L. A., Ludwig, G. V., and Smith, J. F. (1999). *Vaccine* 17(9-10), 1151-60.

Hoke, C. H., Jr. (2005). *Mil Med* 170(4 Suppl), 92-105.

Hunt, A. R., Frederickson, S., Hinkel, C., Bowdish, K. S., and Roehrig, J. T. (2006). *J Gen Virol* 87(Pt 9), 2467-76.

Long, M. C., Jager, S., Mah, D. C., Jebailey, L., Mah, M. A., Masri, S. A., and Nagata, L. P. (2000a). *Hybridoma* 19(1), 1-13.

Long, M. C., Nagata, L. P., Ludwig, G. V., Alvi, A. Z., Conley, J. D., Bhatti, A. R., Suresh, M. R., and Fulton, R. E. (2000b). *Hybridoma* 19(2), 121-7.

Lukaszewski, R. A., and Brooks, T. J. (2000). *J Virol* 74(11), 5006-15.

Mathews, J. H., and Roehrig, J. T. (1982). *J Immunol* 129(6), 2763-7.

Nagata, L. P., Hu, W. G., Masri, S. A., Rayner, G. A., Schmaltz, F. L., Das, D., Wu, J., Long, M. C., Chan, C., Proll, D., Jager, S., Jebailey, L., Suresh, M. R., and Wong, J. P. (2005). *Vaccine* 23(17-18), 2280-3.

Nagata, L. P., Hu, W. G., Parker, M., Chau, D., Rayner, G. A., Schmaltz, F. L., and Wong, J. P. (2006). *J Gen Virol* 87(Pt 8), 2353-61.

Netolitzky, D. J., Schmaltz, F. L., Parker, M. D., Rayner, G. A., Fisher, G. R., Trent, D. W., Bader, D. E., and Nagata, L. P. (2000). *J Gen Virol* 81(Pt 1), 151-9.

Paessler, S., Ni, H., Petrakova, O., Fayzulin, R. Z., Yun, N., Anishchenko, M., Weaver, S. C., and Frolov, I. (2006). *J Virol* 80(6), 2784-96.

Perkins, S. D., O'Brien, L. M., and Phillpotts, R. J. (2006). *Vaccine* 24(17), 3440-5.

Phillpotts, R. J. (2006). *Virus Res* 120(1-2), 107-12.

Phillpotts, R. J., Jones, L. D., and Howard, S. C. (2002). *Vaccine* 20(11-12), 1497-504.

Phillpotts, R. J., O'Brien, L., Appleton, R. E., Carr, S., and Bennett, A. (2005). *Vaccine* 23(13), 1615-23.

Puig-Basagoiti, F., Tilgner, M., Forshey, B. M., Philpott, S. M., Espina, N. G., Wentworth, D. E., Goebel, S. J., Masters, P. S., Falgout, B., Ren, P., Ferguson, D. M., and Shi, P. Y. (2006). *Antimicrob Agents Chemother* 50(4), 1320-9.

Reisen, W. K., and Monath, T. P. (1989). In "The arboviruses: epidemiology and ecology" (T. P. Monath, Ed.), Vol. V, pp. 89-137. CRC Press, Boca Raton, Fla.

Schlesinger, S., and Schlesinger, M. J. (2001). 4th Edition ed. In "Fields Virology" (D. M. Knipe, and P. M. Howley, Eds.), Vol. 2, pp. 2265-2300. 2 vols. Lippincott Williams & Wilkins, Philadelphia.

Seyhan, A. A., Vitiello, D., Shields, M. T., and Burke, J. M. (2002). *J Biol Chem* 277(29), 25957-62.

Sidwell, R. W., and Smee, D. F. (2003). *Antiviral Res* 57(1-2), 101-11.

Strauss, J. H., and Strauss, E. G. (1994). *Microbiol Rev* 58(3), 491-562.

Towbin, H., Staehelin, T., and Gordon, J. (1979). *Proc Natl Acad Sci USA* 76(9), 4350-4.

van Pesch, V., Lanaya, H., Renauld, J. C., and Michiels, T. (2004). *J Virol* 78(15), 8219-28.

Waarts, B. L., Aneke, O. J., Smit, J. M., Kimata, K., Bittman, R., Meijer, D. K., and Wilschut, J. (2005). *Virology* 333(2), 284-92.

Weaver, S. C., Salas, R., Rico-Hesse, R., Ludwig, G. V., Oberste, M. S., Boshell, J., and Tesh, R. B. (1996). *Lancet* 348(9025), 436-40.

Wong, J. P., Nagata, L. P., Christopher, M. E., Salazar, A. M., and Dale, R. M. (2005). *Vaccine* 23(17-18), 2266-8.

Yamamoto, K., Hashimoto, K., Chiba, J., and Simizu, B. (1985). *J Virol* 55(3), 840-2.

SUMMARY OF THE INVENTION

The present invention is directed to the methods of rapidly preventing alphavirus-induced encephalitides pre- or post-exposure to alphaviruses. More specifically, the pre-exposure prevention includes a single dose administration of recombinant adenovirus (Ad) vectors expressing IFN-α or a single dose administration of recombinant Ad vectors expressing the envelope proteins of alphaviruses or a single-dose, simultaneous administration of recombinant Ad vectors expressing IFN-α and recombinant Ad vectors expressing the envelope proteins of alphaviruses. Alternatively, the rapid protection can be achieved by a single dose administration of recombinant Ad vectors co-expressing both IFN-α and the envelope proteins of alphaviruses. Through this approach, a protection response against alphavirus-induced encephalitides can be elicited less than a week after the administration of the recombinant Ad vectors.

The post-exposure protection includes a single dose administration of recombinant Ad vectors expressing IFN-α or a single dose administration of recombinant Ad vectors expressing the envelope proteins of alphaviruses or a single-dose, simultaneous administration of recombinant Ad vectors expressing IFN-α and recombinant Ad vectors expressing the envelope proteins of alphaviruses. Alternatively, the protection can be obtained by a single dose administration of recombinant Ad vectors co-expressing both IFN-α and the envelope proteins of alphaviruses, in which IFN-α expressed by the recombinant Ad vectors first rapidly inhibits the replication of alphaviruses; then this inhibition is enhanced and prolonged by specific immune responses elicited by the envelope proteins expressed from second or the same recombinant Ad vectors.

Accordingly, an embodiment of the present invention provides a method of rapidly (less than a week) preventing a susceptible animal from alphavirus-induced encephalitides before the animal is exposed to alphaviruses by the administration of a single-dose, fast-acting vaccine comprising recombinant viral vectors expressing the structural proteins of alphaviruses or by the administration of a single-dose recombinant viral vectors expressing IFN-α. Alternatively, the rapid pre-exposure protection can be achieved by a single-dose, simultaneous administration of the vaccine and the IFN-α delivered by the recombinant viral vectors or by a single-dose administration of recombinant viral vectors co-expressing both the structural proteins of alphaviruses and IFN-α.

Another embodiment of the present invention provides a method of protecting a susceptible animal from alphavirus-induced encephalitides after the animal is exposed to alphaviruses by the administration of a single-dose, fast-acting vaccine comprising recombinant viral vectors expressing the structural proteins of alphaviruses or by the administration of a single-dose recombinant viral vectors expressing IFN-α. Alternatively, the rapid post-exposure protection can be achieved by a single-dose, simultaneous administration of the vaccine and the IFN-α delivered by the recombinant viral vectors or by a single-dose administration of recombinant viral vectors co-expressing both the structural proteins of alphaviruses and IFN-α.

BRIEF DESCRIPTION OF THE DRAWINGS

FIG. 2 shows three major steps for the assembly of the gene encoding the envelope proteins of the 71V-1658 strain of WEEV. The gene encoding the envelope protein E3-E2 was first cloned by polymerase chain reaction (PCR) into a plasmid through TOPO cloning. The DNA fragment encoding E3-E2 was verified via DNA sequencing, digested with restriction enzymes and ligated with the DNA fragment encoding the envelope protein 6K-E1. The plasmid pcD3-WEEV was used to make a full-length infectious Ad5 clone pAd5-WEEV. The virus derived from this plasmid is named Ad5-WEEV.

FIG. 3 shows the characterization of Ad5-mIFNα expressing mouse IFN-α. Panel A shows a schematic diagram of the viral genome of Ad5-mIFNα. The length of the viral genome (in pink color) is 31,686 bp with deletions in E1 and E3 regions (ΔE1 and ΔE3). The left and right inverted terminal repeats were shown as filled black boxes at the both ends of the genome. A mouse IFN-α expression cassette is composed of $P_{CMV}$ (cytomegalovirus immediate-early promoter; in dark brown), the mouse IFN-α coding region (in dark green), and $P_A$ (SV40 polyadenylation signal; in dark blue). The primers used for PCR amplification of the mouse IFN-α gene is shown as filled black arrows. Panel B shows the detection of the mouse IFN-α gene in the viral genome of Ad5-mIFNα. The mouse IFN-α gene was amplified by PCR using the viral DNA extracted from the purified viral DNA of Ad5-mIFNα (lane 2) or Ad5-EGFP, a control Ad5 vector expressing enhanced green fluorescence protein (EGFP) (lane 3). The PCR products were analyzed on a 0.8% agarose gel. Lane 1, 1 kb DNA Ladder (Sigma). Panel C shows the expression of mouse IFN-α by Ad5-mIFNα. Proteins from the supernatants of mock-infected (lane 3), or Ad5-EGFP-infected (lane 4), or Ad5-mIFNα-infected (lane 5) 293 cells were harvested at 48 hr post-infection and separated by 12% SDS-PAGE. The electrophoresed proteins were visualized by staining the gel with SimplyBlue SafeStain (Invitrogen). Lane 1, MultiMark Multi-Colored protein standard (Invitrogen). Lane 2, empty lane (the band in this lane is due to the spillover of the sample from the lane 3). Panel D shows the detection of mouse IFN-α expressed from Ad5-mIFNα by Western blot. Proteins from the supernatants collected from mock-infected 293 cells (lanes 3, and 6), or 293 cells after 24 hr and 48 hr post-infection with Ad5-EGFP (lanes 4, 5), or 293 cells after 24 hr and 48 hr post-infection with Ad5-mIFNα (lanes 7 and 8) were harvested and separated by 12% SDS-PAGE. The electrophoresed proteins were transferred to a nitrocellulose membrane and probed by rabbit polyclonal antibodies against mIFN-α (Calbiochem). Lane 1, MultiMark Multi-Colored standard (Invitrogen); Lane 2, the recombinant mouse IFN-α produced in E. coli (Calbiochem).

FIG. 4 shows the characterization of Ad5-WEEV expressing the envelope proteins (E3-E2-6K-E1) of the 71V-1658 strain of WEEV. Panel A shows the schematic representation of the expression cassette for the envelope proteins of WEEV cloned in Ad5 vectors. $P_{CMV}$: the immediate-early promoter of human cytomegalovirus; $P_A$: the polyadenylation signal of simian virus 40; ΔE1 and ΔE3: deletions in E1 and E3 genes of the Ad5 genome. Panel B shows the PCR detection of the gene encoding E3-E2-6K-E1 in Ad5-WEEV. Lane 1, Invitrogen high DNA mass ladder; Lane 2, the PCR product from the amplification of Ad5-WEEV. Panel C shows the Western blot detection of the E1 and E2 proteins expressed from Ad5-WEEV. Proteins extracted from 293 cells mock-infected (lanes 2 and 6), or infected with Ad5-EGFP (lanes 3 and 7), or infected with Ad5-WEEV (lanes 4 and 8) were separated by 10% SDS-PAGE. The electrophoresed proteins were transferred to a nitrocellulose membrane and probed with 11D2 mAb specific for E1 and 3F3 mAb specific for E2. Lane 1, MultiMark Multi-Colored standard (Invitrogen).

FIG. 5 shows the post-exposure protection of mice against WEEV infection after co-administration of Ad5-mIFNα expressing mouse IFN-α and Ad5-WEEV expressing the envelope proteins of WEEV. Panel A shows the percentage of survival of mice injected with Ad5-mIFNα and Ad5-WEEV after intranasal challenge with the Fleming strain of WEEV. Panel B shows the severity of the WEEV infection after the WEEV Fleming challenge of mice injected with different combinations of Ad5-mIFNα and Ad5-WEEV or Ad5-EGFP and phosphate-buffered saline (PBS) controls. Mice were scored daily for 4 days after the challenge for the severity of the infection based on the following scale: 0, normal; 1, slightly ruffled hair, very active, no visible signs of infection; 2, very ruffled hair, definite signs of infection, not as active, but still fairly mobile; 3, very ruffled hair, hunched posture, reduced mobility; and 4, very ruffled hair, hunched posture, little or no mobility, rapid breathing. Panel C shows the severity of the WEEV infection after the WEEV Fleming challenge of mice injected with Ad5-mIFNα only and co-injected with Ad5-WEEV and Ad5-mIFNα. The mice were monitored daily for 14 days after the challenge for the severity of the infection by the scoring system described in Panel B.

FIG. 6 shows the pre-exposure protection of mice against WEEV infection after the administration of Ad5-mIFNα expressing mouse IFN-α or Ad5-WEEV expressing the envelope proteins of the 71V-1658 strain of WEEV. Panel A shows the percentage of survival of mice injected intramuscularly (IM) or intranasally (IN) with Ad5-mIFNα after intranasal challenge with 71V-1658. Panel B shows the percentage of survival of mice injected IM with Ad5-WEEV after intranasal challenge with 71V-1658. Mice were scored daily for 14 days after the challenge for the severity of the infection based on the scoring system as described in the legend of FIG. 5.

DETAILED DESCRIPTION OF THE PREFERRED EMBODIMENTS

Figure 1:
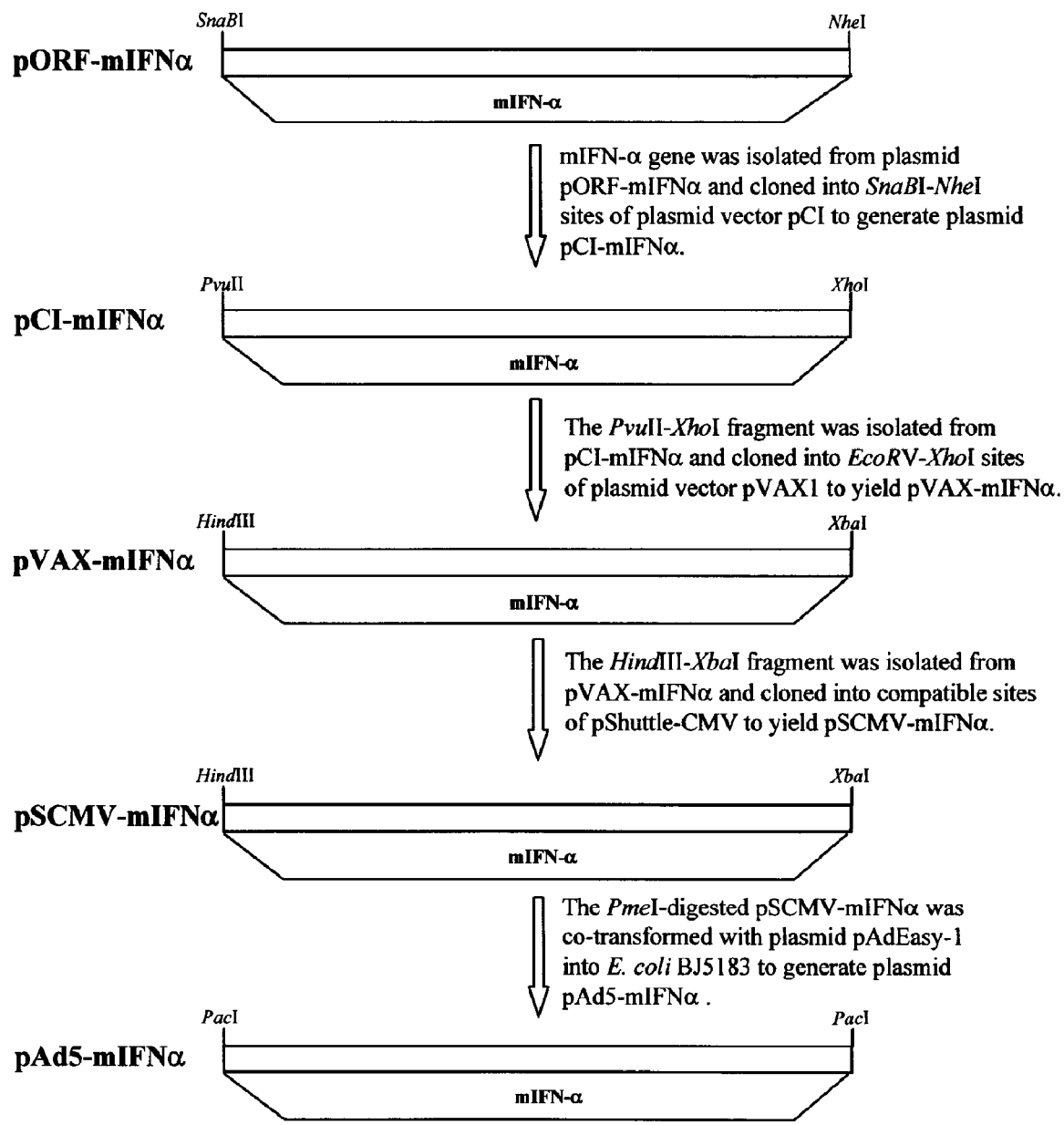
FIG. 1 shows detailed steps for the construction of plasmid pAd5-mIFNα. The gene encoding mouse IFN-α was inserted into the DNA genome of human adenovirus serotype 5 (Ad5) through the homologous recombination in *Escherichia coli* (*E. coli*). The virus derived from this plasmid is named Ad5-mIFNα.

Viruses are extremely simple microorganisms that grow and multiply only in living cells. To start infection, viruses bind to the cells through receptors and inject their genes into the cells to initiate a cascade of gene expressions, which lead to the assembly of new viral particles. Because viruses are highly efficient for delivering their genes into the cells, they have been modified as vectors for the expression of foreign genes in animals. To engineer a virus as a gene delivery vector, a foreign gene is inserted into a region within the viral genome. The insertion of the gene into the viral genome disrupts essential viral genes required for virus replication. Thus, the engineered virus causes dead-end infection in which the virus is able to bind to the cells and to deliver the foreign gene into the cells but is unable to produce new viral particles.

Adenoviruses (Ad) have been extensively used as viral vectors for gene delivery and vaccine development. Ad vectors can deliver therapeutic proteins such as IFN-α to combat viral infections. Ad-mediated expression of IFN-α works as infusion pumps constantly producing IFN-α in animals over the lifespan of Ad vectors and avoids multiple injections of IFN-α. To develop Ad-based vaccines, the gene encoding a heterologous antigen can be delivered and expressed by Ad vectors in animals, resulting in the induction of immune responses. Ad vectors have been used to make the vaccine candidates for VEEV. Ad-vectored VEEV vaccines prevented mice from the aerosol challenge of VEEV when used alone (Phillpotts et al., 2005) or combined with a DNA vaccine (Perkins, O'Brien, and Phillpotts, 2006); however, there is no report on post-exposure protection against VEEV by using these vaccines. Also there have been no reports on Ad-vectored vaccines for WEEV or EEEV.

The present invention uses WEEV as a model pathogen of alphaviruses to demonstrate that co-administration of Ad vectors expressing IFN-α and the envelope proteins of WEEV protects mice from encephalitis after exposure to the virus.

Figure 2:
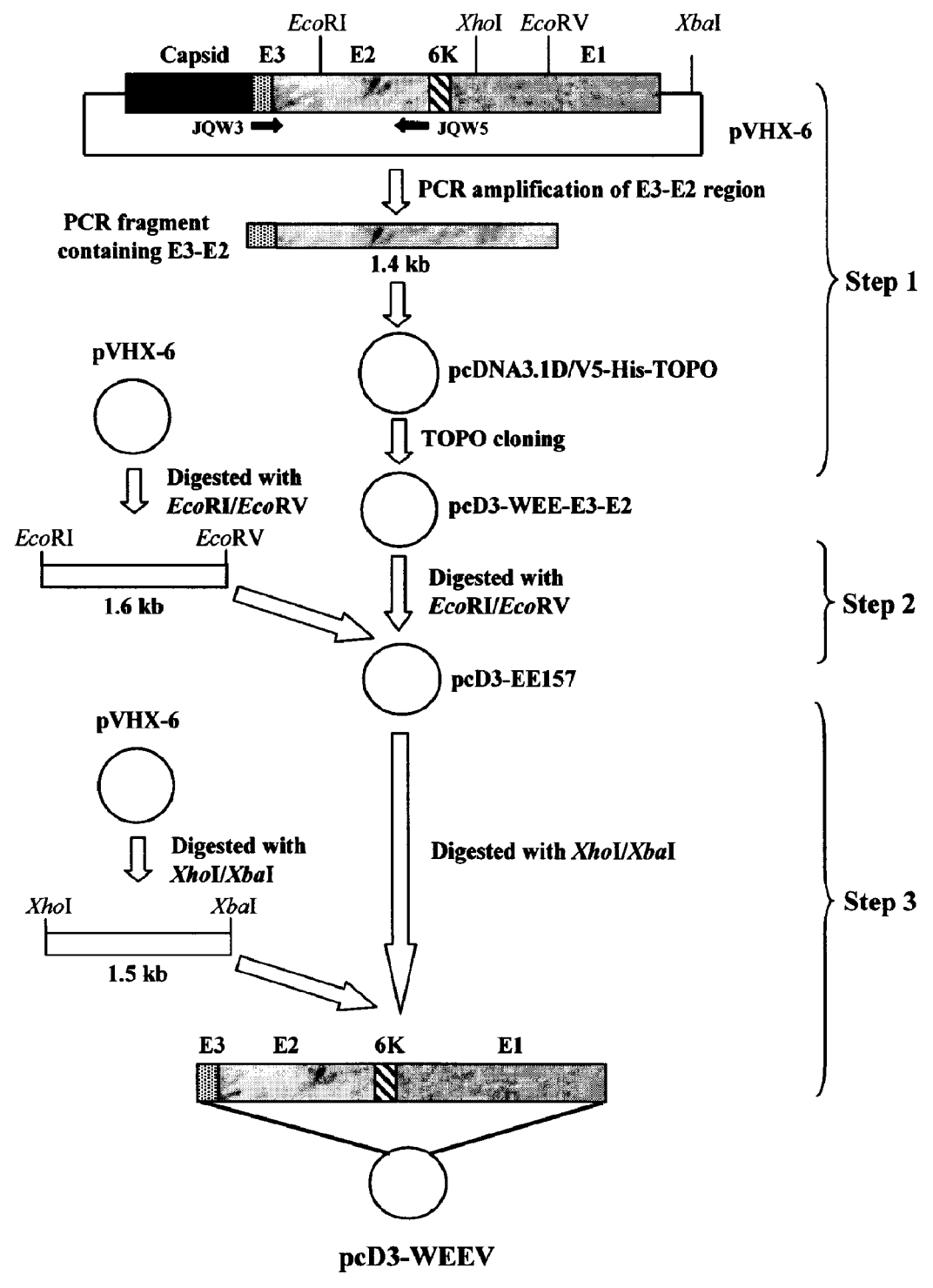

To construct Ad vectors expressing IFN-α or the envelope proteins of the 71-1658 strain of WEEV, the inventors of the present invention made infectious human adenovirus type 5 (Ad5) plasmids containing an expression cassette either for mouse IFN-α or the envelope proteins using a homologous recombination method described in literatures (Chartier et al., 1996; He et al., 1998) (FIG. 1; FIG. 2). The expression cassette contains the immediate-early promoter of cytomegalovirus (CMV), the gene encoding mouse IFN-α or the WEEV envelope proteins, and a simian virus 40 (SV40) polyadenylation signal. The expression cassette was placed in the E1 region of Ad5 between nucleotide (nt) 400 and 1,918 of the viral genome (FIG. 3, Panel A; FIG. 4, Panel A). The placement of the cassette in the E1 region renders the Ad5 vectors replication defective. The full-length infectious Ad5 plasmids were transfected into 293 cells to generate Ad5 vectors designated as Ad5-mIFNα and Ad5-WEEV.

Polymerase chain reaction (PCR) was used to amplify the entire coding region of mouse IFN-α to make sure that the mouse IFN-α gene is present in the viral DNA genome of Ad5-mIFNα. After amplification, the PCR product was separated on agarose gel and visualized with ethidium bromide staining. FIG. 3, Panel B shows that a DNA band corresponding to the size (569 bp) of the mouse IFN-α gene appears in the PCR reaction of Ad5-mIFNα (lane 2). This band was specific for Ad5-mIFNα because no such band can be seen in the PCR reaction of the control vector Ad5-EGFP (lane 3). This result confirms the presence of the mouse IFN-α gene in Ad5-mIFNα.

Having demonstrated that the mouse IFN-α gene was present in the viral genome of Ad5-mIFNα, the inventors of the present invention next want to know whether mouse IFN-α could be expressed in cells infected with Ad5-mIFNα. To do this, 293 cells were mock-infected or infected with Ad5-EGFP, or Ad5-mIFNα. After 48 h post infection, cell culture supernatants were collected and analyzed by electrophoresis in 12% polyacrylamide gel containing sodium dodecyl sulfate (SDS-PAGE). After the electrophoresis, the gel was stained by Coomassie blue. As shown in FIG. 3, Panel C, a band corresponding to the molecular mass of 24 kilodalton (kDa) was shown in the supernatant of 293 cells infected with Ad5-mIFNα (lane 5, indicated by black arrow). The 24-kDa band was absent in the supernatant of mock-infected (lane 3) or Ad5-EGFP-infected 293 cells (lane 4), suggesting that the band was specific for the Ad5-mIFNα-infected cells.

Western blot was carried out to determine whether the 24-kDa protein band is mouse IFN-α. 293 cells were mock-infected, infected with Ad5-EGFP, or Ad5-mIFNα. At 24 and 48 h post infection, cell culture supernatants were collected and subjected to 12% SDS-PAGE. The electrophoresed proteins were transferred to a nitrocellulose membrane and probed with rabbit polyclonal antibodies against mouse IFN-α. FIG. 3, Panel D shows the antibodies recognized a broad protein band with the molecular mass around 24 kDa in supernatants collected from 293 cells after 24 h (lane 7) and 48 h (lane 8) infection with Ad5-mIFNα. No such protein band was detected in mock-infected (lanes 3 and 6) or Ad5-EGFP-infected 293 cells (Lanes 4 and 5). These results confirmed that the 24-kDa protein band from Ad5-mIFNα-infected cells is mouse IFN-α and the molecular mass was consistent with the previous findings (van Pesch et al., 2004). The molecular mass of the mouse IFN-α expressed from Ad5-mIFNα-infected cells (lanes 7 and 8) is larger (24 kDa) than that of the mouse IFN-α expressed in $E.$ $coli$ (lane 2; 19 kDa). As previously reported (van Pesch et al., 2004), the larger molecular mass of the mouse IFN-α expressed from mammalian cells is due to the glycosylation of the protein, which is absent in the $E.$ $coli.$ expression system. Taken together, the inventors of the present invention demonstrated that the mouse IFN-α gene was inserted into the Ad5 genome and mouse IFN-α was produced from the cells infected with Ad5-mIFNα.

The presence of the gene encoding the envelope proteins of the 71V-1658 strain of WEEV in Ad5-WEEV was also verified by PCR. The entire coding region of the envelope protein E3-E2-6K-E1 was amplified and the PCR product was separated on agarose gel and visualized with ethidium bromide staining. FIG. 4, Panel B shows that a DNA band corresponding to the size (2.9 kb) of the entire coding region of E3-E2-6K-E1 appears in the PCR reaction of Ad5-WEEV (lane 2), indicating the presence of the E3-E2-6K-E1 gene in the Ad5-WEEV genome.

Western blot was used to confirm the expression of the envelope proteins from Ad5-WEEV. 293 cells were mock-infected, or infected with Ad5-EGFP or with Ad5-WEEV. At 24 h post infection, cell lysates were collected and subjected to 10% SDS-PAGE. The electrophoresed proteins were transferred to a nitrocellulose membrane and probed, respectively, with 11D2 mAb specific for the E1 envelope protein of WEEV and 3F3 mAb specific for the E2 envelope protein (Long et al., 2000b). 11D2 mAb reacted with a protein band with the molecular mass of approximate 47 kDa in the cells infected with Ad5-WEEV (FIG. 4, Panel C, lane 4). Similarly, 3F3 mAb reacted with a protein band with the molecular mass of approximate 47 kDa in the lysates collected from Ad5-WEEV-infected cells (FIG. 4, Panel C, lane 8). No such protein bands showed in mock-infected (FIG. 4, Panel C, lanes 2 and 6) or Ad5-EGFP-infected 293 cells (FIG. 4, Panel C, lanes 3 and 7). The 47-kDa protein band detected by 11D2 or 3F3 is consistent with the molecular mass of the E1 or E2 envelope protein of WEEV 71V-1658 strain (Das et al., 2004; Long et al., 2000b).

To determine if Ad5-WEEV can induce immune responses in animals, the inventors of the present invention examined neutralizing antibodies against WEEV in sera collected from the mice immunized with Ad5-WEEV. A group of 6 mice were each injected intramuscularly (IM) with $10^7$ pfu of Ad5-WEEV and boosted 4 weeks later by the same dose of Ad5-WEEV. As controls, 3 groups of mice containing 6 mice each were each given PBS, a killed WEE vaccine (Bartelloni et al., 1971), or Ad5-EGFP. Sera from naïve mice and from mice 11 days after each inoculation were collected and neutralizing antibodies against WEEV in pooled sera from each group were detected by a plaque reduction neutralization (PRN) assay. The mice that received Ad5-WEEV developed the WEEV-neutralizing antibodies at a titer of 1:20 after the first injection. After booster, the titers of the neutralizing antibodies were increased by 8-fold (1:160). No WEEV-neutralizing antibodies were detected in sera from the mice inoculated with PBS, the killed WEE vaccine or Ad5-EGFP. These results demonstrated that the humoral immune response was induced after a single dose injection of Ad5-WEEV and the response could be enhanced after the booster.

Figure 5:
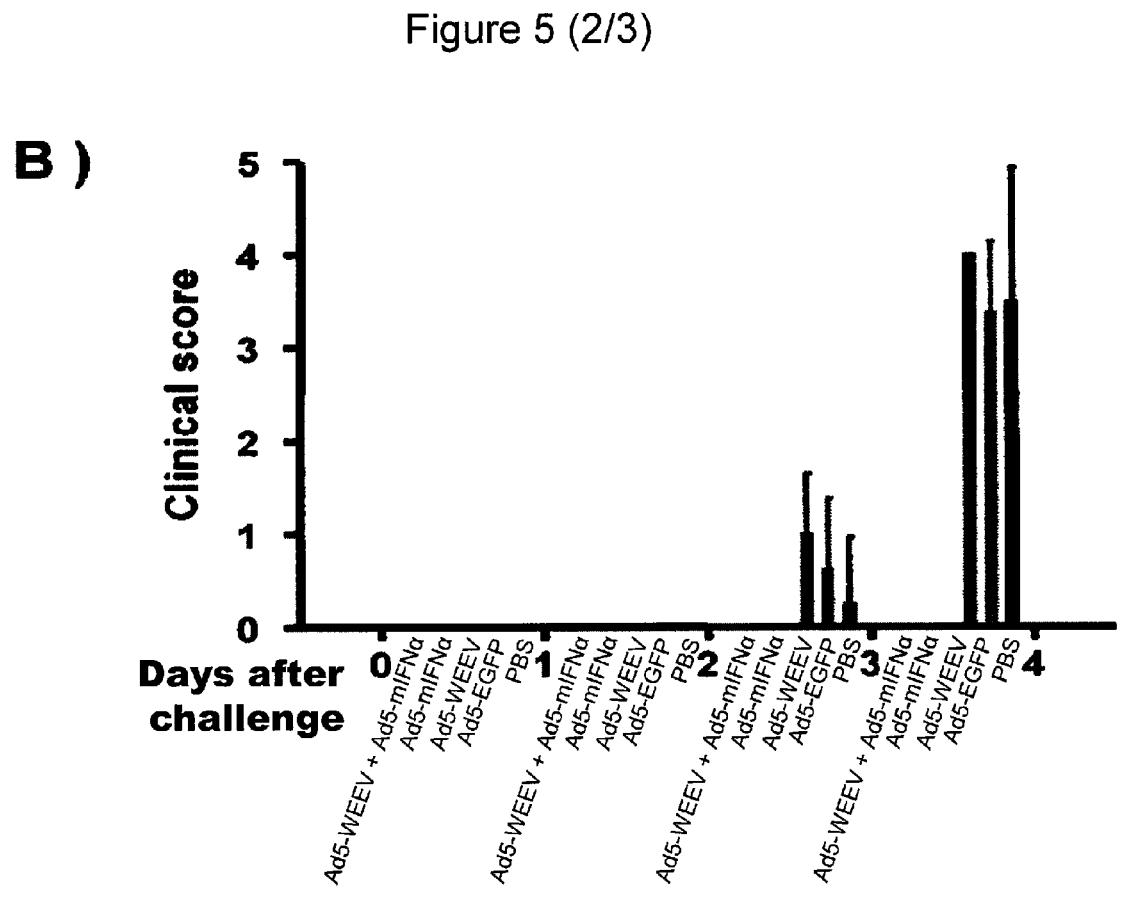

The inventors of the present invention next determined if the co-administration of the Ad vectors expressing mouse IFN-α and the WEEV envelope proteins could protect mice from the WEEV infection after exposure to the virus. Mice were first challenged intranasally (IN) with $1.5\times10^3$ pfu of the Fleming strain of WEEV. At 6 h after the virus challenge, mice were given $10^7$ pfu of Ad5-WEEV only, or $10^7$ pfu of Ad5-mIFNα only, or $10^7$ pfu of Ad5-WEEV and $10^7$ pfu of Ad5-mIFNα. As controls, two groups of mice were injected with PBS or Ad5-EGFP. For the mice challenged with the Fleming strain of WEEV and subsequently inoculated with both Ad5-WEEV and Ad5-mIFNα, 7 of 8 mice were survived (FIG. 5, Panel A). Three of mice in this group showed signs of infection at day 6, 7 and 8 after challenge (FIG. 5, Panel C); however, by day 9, all the mice except one were completely recovered. In the group inoculated with Ad5-mIFNα, 4 of 8 mice showed sighs of infection by day 7 after challenge and never recovered (FIG. 5, Panel C). Three of these 4 sick mice were dead at day 11, 13 and 14 after challenge (FIG. 5, Panel A). In contrast, 7 of 8 mice inoculated with Ad5-WEEV only were all dead by day 4 after challenge (FIG. 5, Panel A). Similarly, all the mice in control groups that were given PBS or Ad5-EGFP were dead by day 4 (FIG. 5, Panel A). Mice in control groups became ill by day 3 after the virus challenge and dead by day 4 (FIG. 5, Panel B). The rapid progress of the infection of the WEEV Fleming strain in the control groups was consistent with our previous observations (Nagata et al., 2006). Therefore, a single dose injection of Ad vectors expressing mouse IFN-α and Ad vectors expressing the envelope proteins of WEEV protected close to 90% of mice from encephalitis after exposure to a lethal dose of WEEV. In contrast, a single dose injection of Ad vectors expressing mouse IFN-α protected only 60% mice from the disease while the administration of Ad vectors expressing the envelope proteins of WEEV has no protection. Therefore, these data demonstrate that co-administration of both Ad vectors is required to achieve protection.

Figure 7:
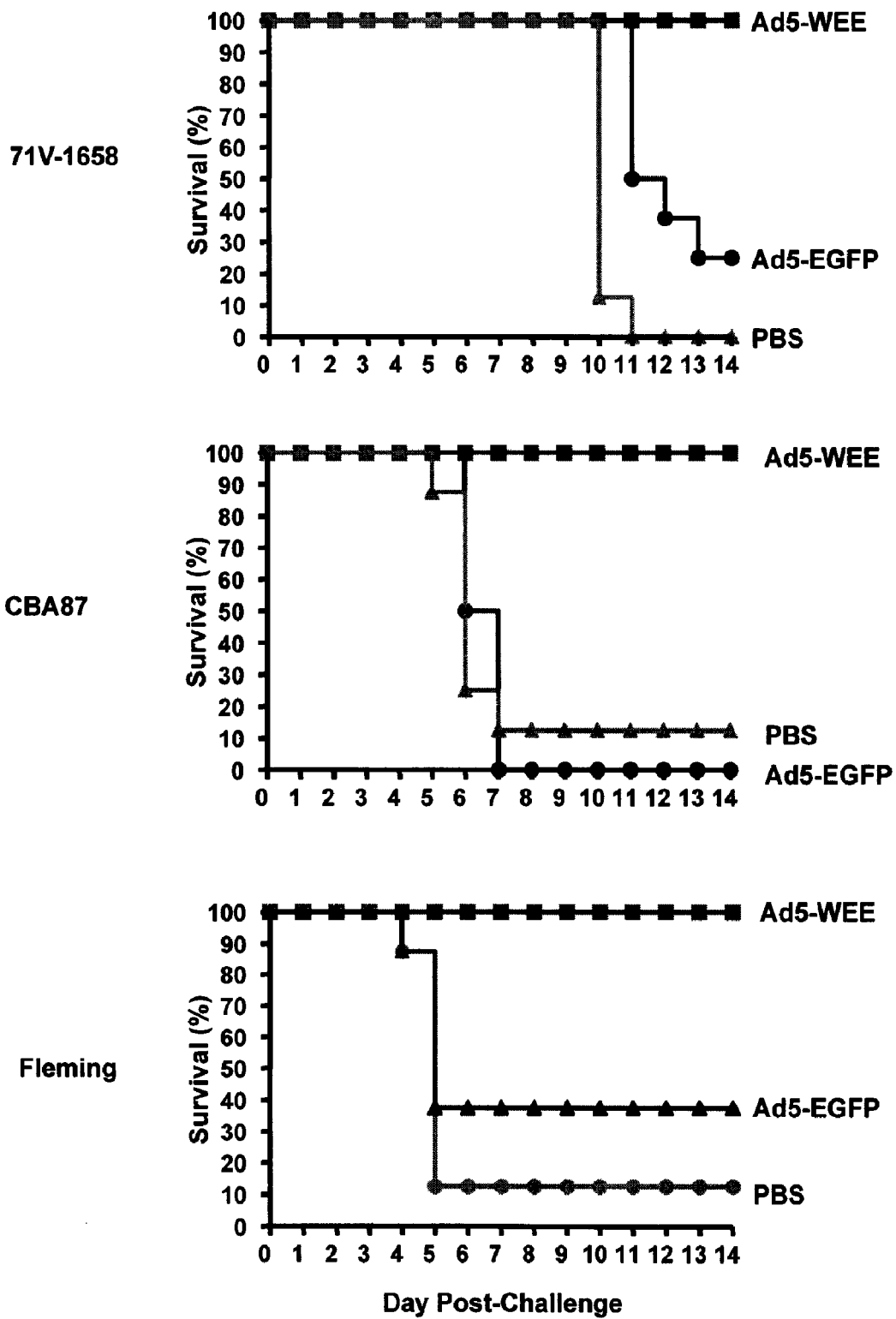
FIG. 7 shows the pre-exposure protection of mice against infections of different WEEV strains after the IM administration of Ad5-WEEV expressing the envelope proteins of the 71V-1658 strain of WEEV. The figure illustrates the percentage of survival of mice injected IM with Ad5-WEEV after intranasal challenge with the WEEV 71V-1658 strain, or the WEEV CBA87 strain or the WEEV Fleming strain. Mice were scored daily for 14 days after the challenge for the severity of the infection.

To determine if the administration of the Ad vectors expressing mouse IFN-α could protect mice from the WEEV infection before exposure to the virus, mice were first injected IM or IN with $10^7$ pfu of Ad5-mIFNα and intranasally (IN) challenged 48 hr later with $1.5 \times 10^3$ pfu of the 71V-1658 strain of WEEV. As controls, groups of mice were injected with PBS or Ad5-EGFP. The mice injected IM or IN with Ad5-mIFNα were all survived (FIG. 6, Panel A). In contrast, less than 50% of mice in PBS control groups and less than 25% of mice in Ad5-EGFP control were survived. In addition, the inventors of the present invention found that the complete protection was obtained in mice that were given Ad5-mIFNα and challenged 1 week later with the 71V-1658 strain of WEEV (data not shown). The rapid pre-exposure protection was also achieved in Ad5-WEEV immunized mice (FIG. 6, Panel B). These mice were first injected IM with $10^7$ pfu of Ad5-WEEV and intranasally (IN) challenged 1 week later with $1.5 \times 10^3$ pfu of the 71V-1658 strain of WEEV. As controls, groups of mice were injected with PBS or Ad5-EGFP. The mice immunized with Ad5-WEEV were all protected. In contrast, almost all the mice in the control groups were dead at day 14 after the challenge (FIG. 6, Panel B). Not surprisingly, mice co-injected with both Ad5-WEEV and Ad5-mIFN-α were also completely protected from the lethal challenge of WEEV within 1 week after injection (data not shown). Additionally, it was found that immunization of mice with Ad5-WEEV one week before challenge is sufficient to protect mice against infections caused by different strains of WEEV (FIG. 7 shows three strains, namely 71V-1658, CBA87 and Fleming). This result suggests that Ad5-WEEV is able to induce a cross-protective immunity against different species of WEEV.

The following examples are aimed to further describe the invention and are not intended to limit the scope of the invention as defined by the claims.

Example 1

Cells and Viruses

Both 293 and Vero cells were purchased from American Type Culture Collection (ATCC, Manassas, Va., USA; catalog number for 293 cells: CRL-1573; catalog number for Vero cells: CCL-81). 293 cells were used to generate, propagate, and titrate the Ad vectors described in the present invention. Vero cells were used for the preparation of WEEV stocks and the detection of WEEV-neutralization antibodies. Both 293 and Vero cells were grown in Dulbecco's modified Eagle medium (D-MEM with high glucose, L-glutamine; Invitrogen/GIBCO, Burlington, ON, Canada) supplemented with 10% defined fetal bovine serum (FBS; HyClone, Mississauga, ON, Canada), 1 mM sodium pyruvate (Invitrogen/GIBCO), and antibiotics-antimycotics (Invitrogen/GIBCO). To propagate the cells, trypsin-EDTA (0.05% Trypsin, EDTA-4Na; Invitrogen/GIBCO) was used to detach adherent cells from the flask. The single cell suspension was diluted at a 1:5 ratio with fresh medium and seeded into new flasks. In addition, a cell bank of 293 cells was established by freezing early passage (passage 4) of cells at $1 \times 10^6$ cells/ml in D-MEM containing 40% FBS, 10% dimethyl sulfoxide (DMSO), 1 mM sodium pyruvate, and antibiotics-antimycotics. 293 cells were used within 30 passages.

The 71V-1658 strain of WEEV contained in a 10% suckling mouse brain suspension was provided by Nick Karabatsos (CDC, Fort Collins, Colo.). The CBA87 strains were kindly provided by Dr George Ludwig (United States Army Medical Research Institute of Infectious Disease, Frederick, Md., USA). The Fleming strain was purchased from ATCC. Seed stocks of WEEV were made by the inoculation of Vero cells with the mouse brain suspension at a multiplicity of infection (MOI) of less than 0.1. The supernatant of the infected cells was collected, aliquoted, and stored at −70° C. for further use in animal challenge study and the plaque reduction neutralization assay. All experiments with WEEV were done in the biological level-3 containment laboratory at Defence Research and Development Canada (DRDC) at Suffield in compliance with the guidelines of Health Canada and Canadian Food Inspection Agency. The Ad vector Ad5-EGFP expressing EGFP was made previously and used as a control.

Example 2

Cloning of the Mouse IFN-α Gene into Ad5 Genome and Generation of Ad5-mIFNα

Plasmid pAd5-mIFNα was constructed and used for generating Ad5 vectors expressing mouse IFN-α. The plasmid was made through the following steps (FIG. 1). First, plasmid pORF-mIFNα (InvivoGen, San Diego, Calif., USA), containing the gene-encoding mouse IFN-α, was digested with restriction enzymes SnaBI and NheI. After electrophoresis of the digested DNA sample on a 0.8% agarose gel, the 736 base pair (bp) DNA fragment containing the mouse IFNα gene was excised from the gel and purified by QIAquick Gel Extraction kit (QIAGEN, Mississauga, ON, Canada). The purified DNA fragment was then cloned into SnaBI-NheI sites of plasmid vector pCI (Promega, Madison, Wis., USA) to yield plasmid pCI-mIFNα. A PvuII-XhoI fragment was isolated from pCI-mIFNα and ligated into EcoRV-XhoI-treated plasmid vector pVAX1 (Invitrogen, Carlsbad, Calif., USA). The resultant plasmid, pVAX1-mIFNα, was cut with HindIII and XbaI and cloned into the compatible sites of plasmid pShuttle-CMV (Qbiogene, Carlsbad, Calif., USA), generating transfer plasmid pSCMV-mIFNα. Finally, the PmeI-digested plasmid pSCMV-mIFNα was mixed with plasmid pAdEasy-1 (Qbiogene), containing a full-length Ad5 genome with deletions in the E1 and E3 regions, and co-transformed into *E. coli* strain BJ5183 (Qbiogene) to produce plasmid pAd5-mIFNα.

For generation of Ad5-mIFNα, 40 μg of plasmid DNA of pAd5-mIFNα, purified by QIAGEN Plasmid Maxi kit (QIAGEN), was digested with restriction enzyme PacI and purified by ethanol precipitation. Then, 8 μg of the digested DNA was incubated with 60 μl of Lipofectamine 2000 (Invitrogen) at room temperature for 20 min. The DNA-Lipofectamine 2000 complexes were added dropwise onto 293 cells seeded in T25 flasks (Corning Inc., Corning, N.Y., USA). Ad5-mIFNα was generated by incubation of the flasks at 37° C. in a $CO_2$ incubator. After the appearance of cytopathic effect (CPE) that was defined by swelling or shrinkage of cells, the formation of multinucleated giant cells (syncytia), and the disintegration of cell monolayer, Ad5-mIFNα was harvested and released from the cells by three cycles of freeze and thaw in a total of 1 ml of D-MEM supplemented with 2% defined fetal bovine serum (FBS), 1 mM sodium pyruvate, and antibiotics-antimycotics. Cell lysates containing Ad5-mIFNα were stored at −70° C.

To propagate Ad5-mIFNα, 293 cells were seeded in five T150 flasks (Corning Inc.) and each flask was inoculated with 100 μl of cell lysate containing Ad5-mIFNα diluted in a total of 5 ml of D-MEM supplemented with 2% defined FBS, 1 mM sodium pyruvate, and antibiotics-antimycotics. After 1 hr incubation at 37° C., an extra 15 ml of D-MEM was added to each flask. Both the cell culture medium and the infected cells were harvested when complete CPE appeared in infected cells. Ad5-mIFNα was purified by BD Adeno-X virus purification kit (BD Biosciences) according to manufacturer's instructions or purified by double cesium chloride (CsCl) gradient centrifugation. The purified Ad5-mIFNα was aliquoted and stored at −70° C.

The titers of the purified Ad5-mIFNα were determined by the tissue culture infectious dose 50 ($TCID_{50}$) assay in 293 cells. To determine the titers of Ad5-mIFNα, 293 cells in D-MEM supplemented with 2% defined fetal bovine serum, 1 mM sodium pyruvate, and antibiotics-antimycotics were seeded into Linbro 96-well flat bottom plates (Flow Laboratories, Inc., McLean, Va., USA) at a concentration of $10^4$ cells per well. A serial of 10-fold dilutions of the purified Ad5-mIFNα was made and 100 μl of the diluted viruses were dispensed into each well. The plate was incubated at 37° C. for 10 days in a $CO_2$ incubator. The number of wells showing CPE was counted and the ratio of CPE wells per row was calculated. $TCID_{50}$ was determined using the following formula: $T=10^{1+d(S-0.5)}$, d=Log 10 of the dilution, S=the sum of ratios in each well. The final titers were converted to pfu/ml by multiplying the $TCID_{50}$ titer by 0.7.

PCR was used to verify the presence of the mouse IFNα gene in the viral genome of Ad5-mIFNα. To do this, viral DNA from purified Ad5-mIFNα was extracted using DNeasy Tissue Kits (QIAGEN) according to manufacture's instructions. Briefly, a total of 200 μl purified virus, containing about $10^7$ pfu of Ad5-mIFNα, was mixed with 20 μl proteinase K and 200 μl Buffer AL. After incubation at 56° C. for 10 min, the sample was mixed with 200 μl pure ethanol and loaded onto DNeasy spin column. The column was washed sequentially with Buffer AW1 and AW2 and the Ad5-mIFNα DNA was eluted from the column with 100 μl $H_2O$.

The purified Ad5-mIFNα DNA was used as a template for PCR. Primers were forward primer JQW7 (5'-GGC TAG GCT CTG TGC TTT CC-3') (SEQ ID NO: I) and reverse primer JQW8 (5'-TCA CTC CTC CTT GCT CAA TC-3') (SEQ ID NO: 2). These primers were designed based on the DNA sequence of Ad5-mIFNα and synthesized by Integrated DNA Technologies, Inc., Coralville, Iowa, USA. PCR was done by PfuTurbo DNA polymerase (Stratagene, La Jolla, Calif., USA) with 2 min of initial denaturation at 95° C., 30 cycles of 30 sec of denaturation at 94° C., 30 sec of annealing at 55° C., and 1 min of extension at 70° C. A final 7 min of extension at 72° C. was carried out after 30 cycles amplification. As a negative control, purified viral DNA from Ad5-EGFP was PCR amplified using the same primers. The PCR products were separated by 0.8% agarose gel and visualized by ethidium bromide staining.

Example 3

Detection of Mouse IFN-α Expressed by Ad5-mIFNα

SDS-PAGE was carried out using the NuPAGE Gel System (Invitrogen) to detect mouse IFN-α expressed by Ad5-mIFNα. To prepare samples for SDS-PAGE, confluent 293 cells seeded in 6-well plates were infected with purified Ad5-EGFP or purified Ad5-mIFNα at an MOI of 1 in a total of 1 ml of D-MEM supplemented with 2% defined FBS, 1 mM sodium pyruvate, and antibiotics-antimycotics. Uninfected 293 cells were included as a negative control. At 48 h post-infection, supernatants (total of 2 ml) from infected cells were collected and concentrated to 250 μl using Amicon Ultra-15 centrifugal filter devices (PL-10, 10,000 NMWL MILLIPORE). A total of 30 μl of the concentrated supernatants was mixed with 10 μl of NuPAGE LDS sample buffer (Invitrogen) containing 5% (V/V) β-mercaptoethanol. The sample was boiled for 5 min, loaded onto NuPAGE Novex 12% Bis-Tris gel along with MultiMark Multi-Colored protein standard (Invitrogen), and electrophoresed at 200 V for 1 h in NuPAGE MOPS SDS running buffer. The electrophoresed proteins were visualized by staining with SimplyBlue SafeStain (Invitrogen).

Mouse IFN-α expressed by Ad5-mIFNα was further confirmed by Western blot, which was carried out by the NuPAGE Gel System and Western Breeze Kit from Invitrogen. To do this, 293 cells seeded in 6-well plates were infected with purified Ad5-EGFP or purified Ad5-mIFNα at an MOI of 1 in a total of 500 μl of D-MEM supplemented with 2% defined FBS, 1 mM sodium pyruvate, and antibiotics-antimycotics. Uninfected 293 cells were included as a negative control. At 24 and 48 h after infection, the medium (total of 500 μl) was collected from each well. A total of 22.5 μl of collected medium was mixed with 7.5 μl of 4× NuPAGE LDS sample buffer containing 5% (V/V) β-mercaptoethanol. As a positive control, 10 μl of purified recombinant mouse IFN-α expressed from E. coli (Calbiochem, Mississauga, Ontario, Canada) was also mixed with the sample buffer. The samples were boiled for 5 min, loaded onto NuPAGE Novex 12% Bis-Tris gel along with MultiMark Multi-Colored protein standard (Invitrogen), and electrophoresed at 200 V for 1 h in NuPAGE MOPS SDS running buffer. The electrophoresed proteins were transferred to a nitrocellulose membrane (Towbin, Staehelin, and Gordon, 1979) at 30 V for 2 h in NuPAGE transfer buffer supplemented with 10% (V/V) methanol using an XCell II Blot Module (Invitrogen). The nitrocellulose membrane was blocked with Blocking Solution and then incubated at room temperature for 1.5 h with rabbit anti-mouse IFNα polyclonal antibodies (Calbiochem) 1:500 diluted in Blocking Solution. The nitrocellulose was rinsed four times with Antibody Wash buffer and incubated for 30 min with goat anti-rabbit, alkaline phosphatase-conjugated antibodies (Invitrogen). Protein bands were visualized by alkaline phosphatase substrate 5-bromo-4-chloro-3-indolyl phosphate (BCIP) and nitro blue tetrazolium (NBT) (Invitrogen).

Example 4

Cloning of the Envelope Protein Gene E3-E2-6K-E1 of WEEV 71V-1658 Strain into Ad5 Genome and Generation of Ad5-WEEV The gene encoding the envelope proteins of the 71V-1658 strain of WEEV was assembled through three steps (FIG. 2). First, the gene encoding the envelope protein E3-E2 was isolated by PCR. To do this, plasmid pVHX-6 (Nagata et al., 2005) was used as a template. Primers for PCR were forward primer JQW3 (5'-CAC CAT GTC ACT AGT TAC AGC GCT ATG CGT GC-3') (SEQ ID NO: 3) and reverse primer JQW5 (5'-TCA CTA AGC GTT GGT TGG CCG AAT GC-3') (SEQ ID NO: 4). These two primers were designed based on the GenBank sequence of 71V-1658 (accession number NC_003908, nt 8250-9698; Netolitzky et al., 2000). A start codon ATG (underlined) was incorporated into the forward primer (JQW3) and stop codons TCACAT (underlined) were built in the reverse primer (JQW5). In addition, four nucleotides CACC (bold) were added at the 5' end of forward primer JQW3 before the ATG start codon to facilitate directional cloning of PCR fragment into TOPO vector. PCR was carried out using PfuTurbo DNA polymerase (Stratagene, La Jolla, Calif., USA) with 2 min of initial denaturation at 95° C., 25 cycles of 30 sec of denaturation at 94° C., 30 sec of annealing at 55° C., as well as 1 min of extension at 70° C. Extension for 7 min of at 72° C. was added as a final step. The 1.4-kb PCR fragment was separated by 0.8% agarose gel and purified by QIAquick Gel Extraction kit (QIAGEN, Mississauga, ON, Canada). The purified PCR fragment was cloned into a linearized plasmid vector pcDNA3.1D/V5-His-TOPO (Invitrogen, Burlington, ON, Canada) to produce plasmid pcD3-WEE-E3-E2. The DNA sequence encoding E3-E2 was verified by DNA sequencing with CEQ8000 Genetic Analysis System (Beckman Coulter INC., Fullerton, Calif., USA).

In the second step of assembly, a 1.6-kb EcoRI-EcoRV fragment, containing the DNA sequence encoding the N-terminal half of the 6K-E1 protein, was isolated from plasmid pVHX-6. The DNA fragment was cloned into plasmid pcD3-WEE-E3-E2 using compatible restriction sites. The resultant plasmid was designated as pcD3-EE157.

In the final step of assembly of the gene encoding the envelope proteins of the 71V-1658 strain, plasmid pVHX-6 was digested with restriction enzymes XhoI and XbaI and a 1.5-kb DNA fragment encoding the C-terminal half of the 6K-E1 protein was isolated. This DNA fragment was then cloned into the XhoI-XbaI sites of plasmid pcD3-EE157 to generate pcD3-WEE-E3-E2-6K-E1 that contains the gene encoding entire E3-E2-6K-E1 polyprotein of 71V-1658.

To insert the gene encoding the E3-E2-6K-E1 of WEEV strain 71V-1658 into the Ad5 genome, a transfer plasmid was made by ligating 3.3-kb HindIII-XbaI fragment isolated from pcD3-WEE-E3-E2-6K-E1 into the HindIII-XbaI sites of plasmid vector pShuttle-CMV (Qbiogene, Carlsbad, Calif., USA). The resultant plasmid, pSCMV-WEE-E3-E2-6K-E1, was linearized with restriction enzyme PmeI and co-transformed with plasmid pAdEasy-1 (Qbiogene) into *E. coli* strain BJ5183 (Qbiogene) to generate pAd5-WEE-E3-E2-6K-E1. The generation, amplification, purification, and titration of Ad5-WEEV were done in similar methods described in Example 2.

To confirm the presence of the gene encoding E3-E2-6K-E1 in Ad5-WEEV, PCR was used to amplify the E3-E2-6K-E1 gene from the Ad5-WEEV DNA extracted from the purified Ad5-WEEV. Primers used for PCR were forward primer S1 (5'-ACC ACG ACC ATG ACA TCA AG-3'$_1$ SEQ ID NO: 5) and reverse primer JQW4 (5'-CCG CGC TCA GTC ATC TAC GTG TG-3'; SEQ ID NO: 6). The primers were synthesized by Integrated DNA Technologies, Inc. (Coralville, Iowa, USA). PCR was done by HotStarTaq DNA polymerase (Qiagene, Mississauga, Ontario, Canada) with an initial activation step of 15 min at 95° C., 30 cycles of 1 min of denaturation at 94° C., 1 min of annealing at 55° C., and 2 min of extension at 72° C. A final 10 min of extension at 72° C. was carried out after 30 cycles of amplification. The DNA fragment obtained by PCR was visualized by ethidium bromide staining after electrophoresis in 0.8% agarose gel.

Example 5

Detection of E1 and E2 Envelope Proteins Expressed by Ad5-WEEV

The expression of E1 and E2 envelope proteins by Ad5-WEEV was detected by Western blot using NuPAGE Gel System and Western Breeze kit from Invitrogen as described in Example 3. 293 cells grown in T25 flasks were infected with purified Ad5-WEEV at an MOI of 1 in a total of 1 ml of D-MEM supplemented with 2% defined FBS, 1 mM sodium pyruvate, and antibiotics-antimycotics. Mock- and Ad5-EGFP-infected 293 cells were included as negative controls. At 24 h after infection, the cell pellets from each infected flask were collected and resuspended in 400 µl of 1×NuPAGE LDS sample buffer containing 5% (V/V) β-mercaptoethanol. The samples were boiled for 5 min and loaded onto 10% Bis-Tris NuPAGE Novex gel along with MultiMark Multi-Colored protein standard (Invitrogen). The protein samples were electrophoresed at 200 V for 1 h in NuPAGE MOPS SDS running buffer. The electrophoresed proteins were transferred to a nitrocellulose membrane at 30 V for 2 h in NuPAGE transfer buffer supplemented with 10% (V/V) methanol using an XCell II Blot Module (Invitrogen). The nitrocellulose membrane was blocked with Blocking Solution and then incubated with 3F3 mAb or 11D2 mAb at room temperature for 1.5 h. 3F3 and 11D2 were previously produced in our laboratory (Long et al., 2000b). 3F3 was raised against the E2 of the B11 strain of WEEV and 11D2 was raised against the E1 of B11. These mAbs also cross-react with the E2 and E1 of the 71V-1658 strain of WEEV. The nitrocellulose membrane was rinsed four times with Antibody Wash buffer and incubated for 30 min with goat anti-mouse, alkaline phosphatase-conjugated antibodies (Invitrogen). Protein bands were visualized using BCIP/NBT substrate for alkaline phosphatase (Invitrogen).

Example 6

Detection of WEEV-Neutralization Antibodies after Administration of Mice with Ad5-WEEV Female BALB/c mice (17-20 g) were obtained from the breeding colony at DRDC-Suffield with the original breeding pairs purchased from Charles River Canada (St. Constant, Quebec). The use of the mice was reviewed and approved by Animal Care Committee of DRDC-Suffield and the guidelines from the Canadian Council on Animal Care were followed for care and handling the mice. Twenty-four mice were divided into 4 groups of 6 mice each. Each mouse was injected intramuscularly (IM) with a total of 100 µl of vaccine preparations into the calf muscle (50 µl on each side). Purified Ad5 vectors were diluted with PBS. Mice in Group 1 were each immunized with $10^7$ pfu of Ad5-WEEV and boosted 4 weeks later with the same dose of Ad5-WEEV. As controls, mice in Group 2 were each injected with $10^7$ pfu of Ad5-EGFP and boosted 4 weeks later with the same dose of Ad5-EGFP. Mice in Group 3 were immunized 3 times (2 weeks apart) with a killed WEE vaccine (Bartelloni et al., 1971). Mice in Group 4 were each injected with 100 µl of PBS. Blood were taken from the tail vein 1 week before injection and 11 days after the first and boost injections and collected into serum separator tubes (Becton Dickinson, Franklin Lakes, N.J., USA). Sera were obtained by centrifugation at 3,300×g for 2 min and stored at −20° C.

Sera collected from the mice were analyzed for the presence of the neutralization antibodies against the 71V-1658 strain by the plaque reduction neutralization (PRN) assay. Pooled sera from each group were heat-inactivated at 56° C. for 30 min. The two-fold diluted sera were mixed with 71V-1658 and incubated at room temperature for 45 min, followed by the inoculation of the mixture into Vero cells seeded in 6-well plates. Neutralizing titers were reported as reciprocals of the highest serum dilution that resulted in a 50% reduction in the number of plaques ($PRN_{50}$) relative to the control Vero cells that were infected with 71V-1658 only.

Example 7

Rapid Post-Exposure Protection of Mice Against WEEV Infection after the Co-Administration of Ad5-mIFNα and Ad5-WEEV Forty female BALB/c mice (17-20 g) were divided into 5 groups of 8 mice each. All the mice were first challenged with the Fleming strain of WEEV through intranasal (IN) inoculation. To do this, mice were anaesthetized with sodium pentobarbital (50 mg/kg body weight, intraperitoneal). When the animals were unconscious, they were carefully supported by hands with their nose up, and a total of $1.5 \times 10^3$ pfu of the virus diluted in 50 μl PBS was gently applied with a micropipette into the nostrils. The applied volume was naturally inhaled into the lungs.

At 6 h after challenge with Fleming, each mouse was injected IM into the calf muscle with a total of 50 μl of purified Ad5 vectors diluted in PBS. Mice in Group 1 were each given $10^7$ pfu of Ad5-EGFP. Mice in Group 2 were each given $10^7$ pfu of Ad5-mIFNα. Mice in Group 3 were each given $10^7$ pfu of Ad5-WEEV. Mice in Group 4 were each given $10^7$ pfu of Ad5-mIFNα and $10^7$ pfu of Ad5-WEEV. As controls, mice in Group 5 were each injected with PBS. Following the injection, mice were examined daily for 14 days for the clinical signs of infection. The following rating scale was used for recording clinical signs: 0, normal; 1, slightly ruffled hair, very active, no visible signs of infection; 2, very ruffled hair, definite signs of infection, not as active, but still fairly mobile; 3, very ruffled hair, hunched posture, reduced mobility; and 4, very ruffled hair, hunched posture, little or no mobility, rapid breathing. Mice scored at the scale of 4 were considered terminally ill and were euthanized by cervical dislocation according to guidelines of the Canadian Council on Animal Care.

Example 8

Rapid Pre-Exposure Protection of Mice Against WEEV Infection after the Administration of Ad5-mIFNα or Ad5-WEEV or Both Forty female BALB/c mice (17-20 g) were divided into 6 groups of 8 mice each. Two groups of mice were each injected intramuscularly (IM) or intranasally (IN) with $10^7$ pfu of Ad5-mIFN-α. Control groups were injected with $10^7$ pfu of Ad5-EGFP or PBS. At 48 hr after injection, all the mice were challenged with the 71V-1658 strain of WEEV through intranasal (IN) inoculation as detailed in Example 7. Following the challenge, mice were examined daily for 14 days for the clinical signs of infection. In another set of experiment, BALB/c mice were divided into 5 groups of 8 mice each. Three groups of mice were each given IM $10^7$ pfu of Ad5-WEEV, or $10^7$ pfu of Ad5-mIFN-α, or $10^7$ pfu of Ad5-WEEV and $10^7$ pfu of Ad5-mIFN-α. As controls, 2 groups of mice were each given $10^7$ pfu of Ad5-EGFP or PBS. One week after the injection, the mice were challenged with the 71V-1658 strain of WEEV. The clinical signs of infection were monitored daily for 14 days following the challenge.

Example 9

Rapid Protection of Mice Against Different Strains of WEEV after the Administration of Ad5-WEEV Seventy-two mice were divided into 9 groups of 8 each. Groups 1, 2, and 3 were each given IM $10^7$ pfu of Ad5-WEEV. As controls, Groups 4, 5, and 6 were each given $10^7$ pfu of Ad5-EGFP and Groups 7, 8, and 9 were each given PBS. At one week after the injection, the mice in Groups 1, 4, and 7 were each challenged IN with $1.5 \times 10^3$ pfu of 71V-1658. Groups 2, 5, and 8 were each challenged IN with $1.5 \times 10^3$ pfu of the Fleming strain. Groups 3, 6, and 9 were each challenged IN with $1.5 \times 10^3$ pfu of the CBA87 strain. Mice were examined daily for 14 days for the clinical signs of infection following the challenge.

From the foregoing, it can be seen that harmless Ad vectors can be used for the delivery of vaccine or IFN-α for pre- and post-exposure protection against alphavirus-induced encephalitides. In this invention, the inventors showed that a single-dose injection of Ad vectors expressing the gene encoding IFN-α or the envelope proteins of alphaviruses or both could protect mice against a lethal dose challenge of the viruses. Ad-vector-mediated expression of IFN-α can last more than a month, thus overcoming the problem of the short half-life of IFN-α. IFN-α expressed from Ad vectors enhances the potency of IFN-α and avoids multiple injections of IFN-α. Furthermore, by delivering the genes encoding the viral proteins into the cells, the Ad vectors elicit a rapid immune response in animals. Since this process is closely mimic natural infection of the viruses, it induces better immune responses when compared to the conventional inactivated or subunit protein vaccines.

It is to be understood that the embodiments and variations shown and described herein are merely illustrative of the principles of this invention and that various modifications may be implemented by those skilled in the art without departing from the scope and spirit of the invention. All documents cited herein are hereby incorporated by reference.

---

What is claimed is:

1. A method for reducing clinical symptoms of a human from alphavirus infection comprising administering a recombinant adenoviral vector comprising a DNA sequence encoding interferon-alpha to the human after exposure to an alphavirus, wherein the administering confers a protective response in the human.

2. The method of claim 1, further comprising administering to said human a recombinant adenoviral vector comprising a DNA sequence encoding the E1 and E2 viral proteins of an alphavirus.

3. The method of claim 1, wherein said alphavirus infection is eastern equine encephalitis virus (EEEV), western equine encephalitis virus (WEEV), Venezuelan equine encephalitis virus (VEEV), or combinations thereof.

4. The method of claim 1, wherein said vector is administered intranasally.

5. A method for conferring a protective response in a human against alphavirus infection comprising administering a recombinant adenoviral vector comprising a DNA sequence encoding interferon-alpha and a recombinant adenovirus vector comprising a DNA sequence encoding the E1 and E2 viral protein of an alphavirus to the human before the alphavirus infection, wherein the administering confers said protective response in the human.

6. The method of claim 5, wherein said alphavirus infection is eastern equine encephalitis virus (EEEV), western equine encephalitis virus (WEEV), Venezuelan equine encephalitis virus (VEEV), or combinations thereof.

* * * * *

UNITED STATES PATENT AND TRADEMARK OFFICE
CERTIFICATE OF CORRECTION

PATENT NO. : 8,303,947 B2  
APPLICATION NO. : 12/545933  
DATED : November 6, 2012  
INVENTOR(S) : Josh Q. Wu et al.

Page 1 of 1

It is certified that error appears in the above-identified patent and that said Letters Patent is hereby corrected as shown below:

On the Title Page, Item [56] under OTHER PUBLICATIONS, in Gowen et al., "Extended Protection...", replace "Consenus" with --Consensus--.

On Title Page 2, Item [56] under OTHER PUBLICATIONS, in Pickles et al., "Retargeting...", replace "Epithetial" with --Epithelial--;

In Pickles et al., "Retargeting...", replace "Adenovirus-Medicated" with --Adenovirus-Mediated--;

In Sumida et al., replace "Anitbodies" with --Antibodies--;

In Zuckerman et al., replace "Cyslic" with --Cystic--.

In the Specifications:

Column 1, Line 34, replace "waling" with --walking--.

Column 10, Line 50, replace "sighs" with --signs--.

Column 13, Line 28, replace "manufacture's" with --manufacturer's--.

Signed and Sealed this  
Second Day of July, 2013

Teresa Stanek Rea  
*Acting Director of the United States Patent and Trademark Office*

SEQUENCE LISTING

```
<160> NUMBER OF SEQ ID NOS: 6

<210> SEQ ID NO 1
<211> LENGTH: 20
<212> TYPE: DNA
<213> ORGANISM: Western equine encephalomyelitis virus
<220> FEATURE:
<221> NAME/KEY: misc_feature
<223> OTHER INFORMATION: PCR primer

<400> SEQUENCE: 1
ggctaggctc tgtgctttcc                                              20
```

```
<210> SEQ ID NO 2
<211> LENGTH: 20
<212> TYPE: DNA
<213> ORGANISM: Western equine encephalomyelitis virus
<220> FEATURE:
<221> NAME/KEY: misc_feature
<223> OTHER INFORMATION: PCR primer

<400> SEQUENCE: 2
tcactcctcc ttgctcaatc                                              20

<210> SEQ ID NO 3
<211> LENGTH: 32
<212> TYPE: DNA
<213> ORGANISM: Western equine encephalomyelitis virus
<220> FEATURE:
<221> NAME/KEY: misc_feature
<223> OTHER INFORMATION: PCR primer

<400> SEQUENCE: 3
caccatgtca ctagttacag cgctatgcgt gc                                32

<210> SEQ ID NO 4
<211> LENGTH: 26
<212> TYPE: DNA
<213> ORGANISM: Western equine encephalomyelitis virus
<220> FEATURE:
<221> NAME/KEY: misc_feature
<223> OTHER INFORMATION: PCR primer

<400> SEQUENCE: 4
tcactaagcg ttggttggcc gaatgc                                       26

<210> SEQ ID NO 5
<211> LENGTH: 20
<212> TYPE: DNA
<213> ORGANISM: Western equine encephalomyelitis virus
<220> FEATURE:
<221> NAME/KEY: misc_feature
<223> OTHER INFORMATION: PCR primer

<400> SEQUENCE: 5
accacgacca tgacatcaag                                              20

<210> SEQ ID NO 6
<211> LENGTH: 23
<212> TYPE: DNA
<213> ORGANISM: Western equine encephalomyelitis virus
<220> FEATURE:
<221> NAME/KEY: misc_feature
<223> OTHER INFORMATION: PCR primer

<400> SEQUENCE: 6
ccgcgctcag tcatctacgt gtg                                          23
```